(12) United States Patent
Djupesland et al.

(10) Patent No.: US 10,478,574 B2
(45) Date of Patent: Nov. 19, 2019

(54) NASAL ADMINISTRATION

(75) Inventors: Per Gisle Djupesland, Oslo (NO); Roderick Peter Hafner, Wiltshire (GB)

(73) Assignee: OptiNose AS, Oslo (NO)

( * ) Notice: Subject to any disclaimer, the term of this patent is extended or adjusted under 35 U.S.C. 154(b) by 2846 days.

(21) Appl. No.: 12/161,466

(22) PCT Filed: Jan. 19, 2006

(86) PCT No.: PCT/GB2006/000182
§ 371 (c)(1),
(2), (4) Date: Feb. 1, 2011

(87) PCT Pub. No.: WO2007/083073
PCT Pub. Date: Jul. 26, 2007

(65) Prior Publication Data
US 2011/0114087 A1 May 19, 2011

(51) Int. Cl.
*H01M 4/86* (2006.01)
*H01M 4/90* (2006.01)
(Continued)

(52) U.S. Cl.
CPC .................................. *A61M 15/08* (2013.01)

(58) Field of Classification Search
CPC ............ A61M 15/002; A61M 15/0091; A61M 15/0098; A61M 15/08; A61M 11/02; A61M 11/08
(Continued)

(56) References Cited

U.S. PATENT DOCUMENTS

| 39,678 A | 8/1863 | Russell |
|---|---|---|
| 605,436 A | 6/1898 | Kellogg |

(Continued)

FOREIGN PATENT DOCUMENTS

| EP | 0341967 | 11/1989 |
|---|---|---|
| GB | 2400565 | 10/2004 |

(Continued)

OTHER PUBLICATIONS

Mathison et al. (Nasal Route for Direct Delivery of Solutes to the Central Nervous System: Fact or Ficton? Journal of Drug Targeting, 1998. vol. 5 No. 6 pp. 415-441.*
(Continued)

*Primary Examiner* — Bhisma Mehta
*Assistant Examiner* — Matthew A Engel
(74) *Attorney, Agent, or Firm* — Finnegan, Henderson, Farabow, Garrett & Dunner, LLP

(57) ABSTRACT

A delivery device for and method of providing for delivery of substance to the central nervous system (CNS) of a subject, the delivery device comprising: a nosepiece unit (17) for insertion into a nasal airway (1) of a subject and comprising an outlet unit (21) which includes a nozzle (25) for delivering substance into the nasal airway of the subject; and a substance supply unit which is operable to deliver a dose of substance to the nozzle: wherein the delivery device is configured such that at least 30% of the dose as initially deposited in the nasal airway is deposited in an upper posterior region of the nasal airway, thereby providing a CNS concentration of the substance, and hence CNS effect, which is significantly greater than that which would be predicted from a counterpart blood plasma concentration of the substance.

39 Claims, 11 Drawing Sheets

(51) Int. Cl.
  *A61M 15/08* (2006.01)
  *H01M 8/023* (2016.01)
  *H01M 8/124* (2016.01)
  *H01M 8/0247* (2016.01)
  *H01M 8/2425* (2016.01)

(58) Field of Classification Search
  USPC ............ 128/203.18, 200.14, 203.12, 203.15,
                    128/203.19, 200.22, 200.23, 204.26;
                    604/93.01, 94.01
  See application file for complete search history.

(56) References Cited

U.S. PATENT DOCUMENTS

| | | | |
|---|---|---|---|
| 642,748 A | 2/1900 | Manners | |
| 746,749 A | 12/1903 | Seidel | |
| 2,223,611 A | 12/1940 | Gross | |
| 2,470,297 A * | 5/1949 | Fields | A61M 15/00 |
| | | | 128/203.15 |
| 3,949,939 A | 4/1976 | Brown | |
| 5,116,311 A | 5/1992 | Löfstedt | |
| 5,558,085 A * | 9/1996 | Rubsamen | A61M 15/0045 |
| | | | 128/200.14 |
| 5,624,898 A * | 4/1997 | Frey, II | A61K 9/0043 |
| | | | 424/400 |
| 5,693,065 A | 12/1997 | Rains, III | |
| 5,797,392 A | 8/1998 | Keldmann et al. | |
| 6,186,141 B1 * | 2/2001 | Pike | A61B 18/12 |
| | | | 128/203.12 |
| 6,386,197 B1 | 5/2002 | Miller | |
| 6,647,980 B1 * | 11/2003 | Gizurarson | A61M 15/0028 |
| | | | 128/200.14 |
| 6,648,848 B1 | 11/2003 | Keldmann et al. | |
| 6,678,553 B2 * | 1/2004 | Lerner | A61K 9/0009 |
| | | | 600/380 |
| 6,715,485 B1 | 4/2004 | Djupesland | |
| D530,815 S | 10/2006 | Murphy et al. | |
| 7,189,753 B1 | 3/2007 | Cady et al. | |
| 7,347,201 B2 | 3/2008 | Djupesland | |
| 7,377,901 B2 | 5/2008 | Djupesland et al. | |
| 7,481,218 B2 | 1/2009 | Djupesland | |
| 7,543,581 B2 | 6/2009 | Djupesland | |
| 7,740,014 B2 | 6/2010 | Djupesland | |
| 7,784,460 B2 | 8/2010 | Djupesland et al. | |
| 7,841,337 B2 | 11/2010 | Djupesland | |
| 7,854,227 B2 | 12/2010 | Djupesland | |
| 7,934,503 B2 | 5/2011 | Djupesland et al. | |
| 7,975,690 B2 | 6/2011 | Djupesland | |
| 8,047,202 B2 | 11/2011 | Djupesland | |
| 8,146,589 B2 | 4/2012 | Djupesland | |
| 8,171,929 B2 | 5/2012 | Djupesland et al. | |
| 8,327,844 B2 | 12/2012 | Djupesland | |
| 8,511,303 B2 | 8/2013 | Djupesland | |
| 8,522,778 B2 | 9/2013 | Djupesland | |
| 8,550,073 B2 | 10/2013 | Djupesland | |
| 8,555,877 B2 | 10/2013 | Djupesland | |
| 8,555,878 B2 | 10/2013 | Djupesland | |
| 8,590,530 B2 | 11/2013 | Djupesland et al. | |
| 8,596,278 B2 | 12/2013 | Djupesland | |
| 8,800,555 B2 | 8/2014 | Djupesland | |
| 8,875,704 B2 | 11/2014 | Djupesland et al. | |
| 8,899,229 B2 | 12/2014 | Djupesland et al. | |
| 8,910,629 B2 | 12/2014 | Djupesland et al. | |
| D723,156 S | 2/2015 | Djupesland et al. | |
| D725,769 S | 3/2015 | Djupesland et al. | |
| 8,978,647 B2 | 3/2015 | Djupesland et al. | |
| 9,010,325 B2 | 4/2015 | Djupesland et al. | |
| 9,038,630 B2 | 5/2015 | Djupesland | |
| 9,067,034 B2 | 6/2015 | Djupesland et al. | |
| 9,072,857 B2 | 7/2015 | Djupesland | |
| 9,108,015 B2 | 8/2015 | Djupesland | |
| 9,119,932 B2 | 9/2015 | Djupesland | |
| 9,132,249 B2 | 9/2015 | Djupesland | |
| 9,144,652 B2 | 9/2015 | Djupesland et al. | |
| 9,168,341 B2 | 10/2015 | Djupesland | |
| 9,205,208 B2 | 12/2015 | Djupesland | |
| 9,205,209 B2 | 12/2015 | Djupesland | |
| 9,272,104 B2 | 3/2016 | Djupesland | |
| 2001/0024641 A1 * | 9/2001 | Yang | A61K 9/1617 |
| | | | 424/46 |
| 2002/0017294 A1 * | 2/2002 | Py | A61M 11/06 |
| | | | 128/200.23 |
| 2003/0015190 A1 | 1/2003 | Rabinowitz et al. | |
| 2003/0121793 A1 * | 7/2003 | Groeger | B05D 7/227 |
| | | | 205/196 |
| 2003/0133877 A1 * | 7/2003 | Levin | A61K 9/0043 |
| | | | 424/45 |
| 2003/0158527 A1 * | 8/2003 | Mezzoli | A61H 35/04 |
| | | | 604/275 |
| 2004/0024330 A1 | 2/2004 | Djupesland et al. | |
| 2004/0112378 A1 * | 6/2004 | Djupesland | A61B 5/085 |
| | | | 128/203.12 |
| 2004/0112379 A1 | 6/2004 | Djupesland | |
| 2004/0112380 A1 | 6/2004 | Djupesland | |
| 2004/0138618 A1 * | 7/2004 | Mazzoni | A61M 15/0028 |
| | | | 604/131 |
| 2004/0149289 A1 | 8/2004 | Djupesland | |
| 2004/0151774 A1 | 8/2004 | Pauletti et al. | |
| 2004/0153033 A1 * | 8/2004 | Mazzoni | A61M 15/0028 |
| | | | 604/192 |
| 2004/0167158 A1 | 8/2004 | Edwards et al. | |
| 2004/0182388 A1 * | 9/2004 | Djupesland | A61M 3/0279 |
| | | | 128/203.15 |
| 2005/0028812 A1 | 2/2005 | Djupesland | |
| 2005/0034723 A1 * | 2/2005 | Bennett | A61K 9/007 |
| | | | 128/203.12 |
| 2005/0072430 A1 | 4/2005 | Djupesland | |
| 2005/0164997 A1 | 7/2005 | Biggadike | |
| 2005/0235992 A1 | 10/2005 | Djupesland | |
| 2006/0096589 A1 | 5/2006 | Djupesland | |
| 2006/0107957 A1 | 5/2006 | Djupesland | |
| 2006/0147389 A1 * | 7/2006 | Staniforth | A61K 9/0073 |
| | | | 424/46 |
| 2006/0169278 A1 | 8/2006 | Djupesland et al. | |
| 2006/0207596 A1 * | 9/2006 | Lane | A61M 11/00 |
| | | | 128/206.11 |
| 2006/0219240 A1 | 10/2006 | Djupesland | |
| 2006/0219241 A1 | 10/2006 | Djupesland | |
| 2006/0225732 A1 | 10/2006 | Djupesland | |
| 2006/0231094 A1 | 10/2006 | Djupesland | |
| 2006/0289007 A1 * | 12/2006 | Williams | A61M 15/0091 |
| | | | 128/203.15 |
| 2007/0031340 A1 * | 2/2007 | Hale | A61K 9/7007 |
| | | | 424/45 |
| 2007/0039614 A1 | 2/2007 | Djupesland | |
| 2007/0125371 A1 | 6/2007 | Djupesland | |
| 2007/0129665 A1 * | 6/2007 | Dickens | A61M 15/0028 |
| | | | 604/26 |
| 2007/0186927 A1 | 8/2007 | Djupesland et al. | |
| 2007/0276024 A1 * | 11/2007 | Bond | A61K 31/135 |
| | | | 514/411 |
| 2008/0161771 A1 | 7/2008 | Djupesland | |
| 2008/0163874 A1 | 7/2008 | Djupesland | |
| 2008/0221471 A1 | 9/2008 | Djupesland et al. | |
| 2008/0223363 A1 | 9/2008 | Djupesland | |
| 2008/0226736 A1 | 9/2008 | Caponetti et al. | |
| 2008/0260848 A1 | 10/2008 | Nagata et al. | |
| 2008/0289629 A1 | 11/2008 | Djupesland | |
| 2009/0101146 A1 | 4/2009 | Djupesland | |
| 2009/0293873 A1 | 12/2009 | Djupesland et al. | |
| 2009/0304802 A1 | 12/2009 | Djupesland et al. | |
| 2009/0314293 A1 * | 12/2009 | Djupesland | A61M 11/00 |
| | | | 128/203.18 |
| 2009/0320832 A1 | 12/2009 | Djupesland | |
| 2010/0035805 A1 | 2/2010 | Hafner | |
| 2010/0051022 A1 | 3/2010 | Djupesland et al. | |
| 2010/0057047 A1 | 3/2010 | Djupesland et al. | |
| 2010/0242959 A1 | 9/2010 | Djupesland et al. | |
| 2010/0282246 A1 | 11/2010 | Djupesland et al. | |
| 2010/0288275 A1 | 11/2010 | Djupesland et al. | |
| 2010/0300439 A1 | 12/2010 | Djupesland et al. | |
| 2011/0023869 A1 | 2/2011 | Djupesland | |

(56) References Cited

U.S. PATENT DOCUMENTS

| | | |
|---|---|---|
| 2011/0053827 A1 | 3/2011 | Hafner |
| 2011/0088690 A1 | 4/2011 | Djupesland et al. |
| 2011/0088691 A1 | 4/2011 | Djupesland |
| 2011/0114087 A1 | 5/2011 | Djupesland et al. |
| 2011/0126830 A1 | 6/2011 | Djupesland et al. |
| 2011/0259329 A1 | 10/2011 | Djupesland et al. |
| 2011/0318345 A1 | 12/2011 | Djupesland |
| 2012/0000459 A1 | 1/2012 | Djupesland |
| 2012/0006323 A1 | 1/2012 | Djupesland |
| 2012/0073571 A1 | 3/2012 | Djupesland |
| 2012/0090608 A1 | 4/2012 | Djupesland et al. |
| 2012/0260915 A1 | 10/2012 | Djupesland |
| 2013/0098362 A1 | 4/2013 | Djupesland et al. |
| 2013/0125889 A1 | 5/2013 | Djupesland et al. |
| 2013/0327320 A1 | 12/2013 | Djupesland |
| 2014/0018295 A1 | 1/2014 | Djupesland |
| 2014/0041660 A1 | 2/2014 | Djupesland et al. |
| 2014/0060536 A1 | 3/2014 | Djupesland |
| 2014/0073562 A1 | 3/2014 | Djupesland |
| 2014/0144442 A1 | 5/2014 | Djupesland et al. |
| 2014/0144443 A1 | 5/2014 | Djupesland et al. |
| 2014/0166008 A1 | 6/2014 | Djupesland |
| 2014/0202456 A1 | 7/2014 | Djupesland |
| 2014/0246022 A1 | 9/2014 | Djupesland et al. |
| 2015/0007811 A1 | 1/2015 | Djupesland et al. |
| 2015/0013670 A1 | 1/2015 | Djupesland et al. |
| 2015/0013677 A1 | 1/2015 | Djupesland et al. |
| 2015/0053201 A1 | 2/2015 | Djupesland et al. |
| 2015/0090259 A1 | 4/2015 | Djupesland et al. |
| 2015/0101605 A1 | 4/2015 | Djupesland et al. |
| 2015/0144129 A1 | 5/2015 | Djupesland et al. |
| 2015/0165139 A1 | 6/2015 | Hafner |
| 2015/0182709 A1 | 7/2015 | Djupesland |
| 2015/0246194 A1 | 9/2015 | Djupesland et al. |
| 2015/0367090 A1 | 12/2015 | Djupesland et al. |
| 2015/0367091 A1 | 12/2015 | Djupesland et al. |
| 2016/0001022 A1 | 1/2016 | Djupesland et al. |
| 2016/0045687 A1 | 2/2016 | Djupesland |
| 2016/0051778 A1 | 2/2016 | Djupesland et al. |
| 2016/0074603 A1 | 3/2016 | Djupesland et al. |
| 2016/0082206 A1 | 3/2016 | Djupesland et al. |
| 2016/0082207 A1 | 3/2016 | Djupesland et al. |

FOREIGN PATENT DOCUMENTS

| | | |
|---|---|---|
| GB | 2 404 867 | 2/2005 |
| WO | WO 96/22802 | 8/1996 |
| WO | WO 98/53869 | 12/1998 |
| WO | 00/051672 | 9/2000 |
| WO | WO 00/51672 | 9/2000 |
| WO | WO 01/97689 | 12/2001 |
| WO | WO 02/068029 | 9/2002 |
| WO | WO 02/068030 | 9/2002 |
| WO | WO 02/068031 | 9/2002 |
| WO | WO 02/068032 | 9/2002 |
| WO | WO 02/083219 A1 | 10/2002 |
| WO | 03/000310 | 1/2003 |
| WO | WO 03/000310 | 1/2003 |
| WO | WO 03/00310 A2 * | 1/2003 |
| WO | WO 03/020350 | 3/2003 |
| WO | WO 03/082393 | 10/2003 |
| WO | WO 03/084591 | 10/2003 |
| WO | WO 03/090812 | 11/2003 |
| WO | WO 2004/004814 | 1/2004 |
| WO | WO 2004/004922 | 1/2004 |
| WO | WO 2004/060433 | 7/2004 |
| WO | WO 2004/103447 | 12/2004 |
| WO | WO 2005/016423 | 2/2005 |
| WO | WO 2005/021059 | 3/2005 |
| WO | WO 2006/030210 | 3/2006 |
| WO | WO 2006/090149 | 8/2006 |
| WO | WO 2007/083073 | 7/2007 |
| WO | WO 2007/093784 | 8/2007 |
| WO | WO 2007/093791 | 8/2007 |
| WO | WO 2007/099361 | 9/2007 |
| WO | WO 2007/102089 | 9/2007 |
| WO | WO 2007/107887 | 9/2007 |
| WO | WO 2007/125318 | 11/2007 |
| WO | WO 2007/141541 | 12/2007 |
| WO | WO 2008/012531 | 1/2008 |
| WO | WO 2008/065403 | 6/2008 |
| WO | WO 2008/081326 | 7/2008 |
| WO | WO 2008/081327 | 7/2008 |
| WO | WO 2008/122791 | 10/2008 |
| WO | WO 2008/122795 | 10/2008 |
| WO | WO 2009/044172 | 4/2009 |
| WO | WO 2010/029441 | 3/2010 |
| WO | WO 2012/035427 | 3/2012 |
| WO | WO 2012/123819 | 9/2012 |
| WO | WO 2013/124491 | 8/2013 |
| WO | WO 2013/124492 | 8/2013 |
| WO | WO 2013/124493 | 8/2013 |
| WO | WO 2014/155192 | 10/2014 |

OTHER PUBLICATIONS

U.S. Appl. No. 12/757,626, Djupesland, filed Apr. 9, 2010.
U.S. Appl. No. 12/303,667, Djupesland, filed Nov. 1, 2010.
U.S. Appl. No. 12/516,399, Djupesland, filed May 21, 2010.
U.S. Appl. No. 12/516,401, Djupesland, filed Jul. 12, 2010.
U.S. Appl. No. 12/681,150, Djupesland et al., filed Dec. 21, 2010.
U.S. Appl. No. 12/871,443, Djupesland et al., filed Aug. 30, 2010.
U.S. Appl. No. 12/955,546, Djupesland, filed Nov. 29, 2010.
U.S. Appl. No. 12/973,317, Djupesland, filed Dec. 20, 2010.
International Search Report for International App. No. PCT/GB2006/000182, dated Apr. 4, 2008 (6 pages).
International Preliminary Report on Patentability for International App. No. PCT/GB2006/000182 (18 pages).
Lars Edvinsson, et al., *Triptan-induced contractile (5-HT1B receptor) responses in human cerebral and coronary arteries: relationship to clinical effect*, 109 Clinical Science 335-342 (2005).
Anthony W. Fox, *Onset Effect of 5-HT1B/1D Agonists: A Model with Pharmacokinetic Validation*, 44 Headache 142-147 ( 2004).
Niels Einer-Jensen, et al., *Intranasal Absorption of Sumatriptan and Naratriptan: No Evidence of Local Transfer from the Nasal Cavities to the Brain Arterial Blood in Male Rats*, 22 Biopharm, Drug Dispos. 213-219 (2001).
Bi-directional nasal drug delivery, Per G. Djupesland and Rod Hafner, Innovations in Pharmaceutical Technology (Jun. 2004).
Cindy H. Dubin, *Nothing to Sneeze At*, Pharmaceutical Formulation & Quality Magazine (Jan. 29, 2003).
Per Gisle Djupesland, *Nasal Delivery of Vaccines*, EPC (Jan. 29, 2003).
Per Gisle Djupesland, *Who Nose How Far Nasal Delivery Can Go?*, EPC (Oct. 7, 2003).
Per Gisle Djupesland, *Bi-directional Nasal Drug Delivery*, Innovations in Pharmaceutical Technology (Jul. 10, 2004).
P.G. Djupesland, *Bi-Directional Nasal Delivery of Aerosols Can Prevent Lung Deposition*, Journal of Aerosol Medicine (Sep. 2004).
*Bi-Directional Nasal Device Delivers Drug on Exhalation*, Pharmaceutical Technology (Sep. 10, 2004).
Ola Dale et al., *Intranasal Midazolam: A Comparison of Two Delivery Devices in Human Volunteers*, Journal of Pharmacy and Pharmacology (Oct. 2004).
M. Kleven, *Using Computational Fluid Dynamics (CFD) to Improve the Bi-Directional Nasal Drug Delivery Concept*, Trans IChemE Part C. (Jun. 2005).
Per Gisle Djupesland, *Breath-Actuated Bi-Directional Delivery Sets the Nasal Market on a New Course*, ONdrugDelivery (Oct. 10, 2005).
Hilde Bakke et al., *Oral Spray Immunization May be an Alternative to Intranasal Vaccine Delivery to Induce Systemic Antibodies But Not Nasal Mucosal or Cellular Immunity*, Scan J. of Immunol. (Mar. 2006).
P.G. Djupesland et al., *Breath Actuated Nasal Device Improves Delivery to Target Sites Beyond the Nasal Valve*, The Laryngoscope (Mar. 2006).

(56) References Cited

OTHER PUBLICATIONS

R. Luthringer et al., *Rapid Absorption of Sumatriptan Powder and Effects on Glyceryl tinitrate Model of Headache Following Intranasal Delivery Using a Novel Bi-Directional Device*, Journal of Pharmacy and Pharmacology (Jan. 2009).

A. Skretting et al., *A New Method for Scintigraphic Quantification of Deposition and Clearance in Anatomical Regions of the Human Nose*, Nuclear Medicine Communications (Aug. 2009).

Vlckovia et al., *Effective Treatment of Mild-to-Moderate Nasal Polyposis with Fluticasone Delivered by a Novel Device*, Rhinology (Oct. 22, 2009).

Per Gisle Djupesland et al., *Impact of Baseline Nasal Polyp Size and Previous Surgery on Efficacy of Fluticasone Delivered With a Novel Device: A Subgroup Analysis*, Am. J. Rhinology Allergy (2010).

P.G. Djupesland et al., *Intranasal Sumatriptan Powder Delivered by a Novel Breath Actuated Bi-Directional Device for the Acute Treatment of Migraine: A Randomised Placebo-Controlled Study*, Cephalalgia (Mar. 17, 2010).

F.S. Hansen et al., *Preliminary Efficacy of Fluticasone Delivered by a Novel Device in Recalcitrant Chronic Rhinosinusitis*, Rhinology (Jun. 26, 2010).

Per Gisle Djupesland, *Nasal Drug Delivery Devices: Characteristics and Performance in Clinical Perspective—A Review*, Drug. Deliv. and Transl. Res. (Oct. 18, 2012).

Per Gisle Djupesland, *Nasal Deposition and Clearance in Man: Comparison of a Bidirectional Powder Device and a Traditional Liquid Spray Pump*, Journal of Aerosol Medicine and Pulmonary Drug Delivery (Nov. 2012).

Stewart J. Tepper, *Clinical Implications for Breath-Powered Powder Sumatriptan Intranasal Treatment*, Headache, The American Headache Society (Apr. 29, 2013).

Mohammad Obaidi et al., *Improved Pharmacokinetics of Sumatriptan With Breath Powered Nasal Delivery of Sumatriptan Powder*, Headache, The American Headache Society (May 24, 2013).

Per Gisle Djupesland, *Breath Powdered Nasal Delivery: A New Route to Rapid Headache Relief*, Headache, The American Headache Society (Jun. 4, 2013).

Per Gisle Djupesland et al., *The Nasal Approach to Delivering Treatment for Brain Diseases: An Anatomic, Physiologic, and Delivery Technology Overview*, Therapeutic Delivery (2014).

R.K. Cady et al., *A Randomized Double-Blind, Placebo Controlled Study of Breath Powered Nasal Delivery of Sumatriptan Powder (AVP-825) in the Treatment of Acute Migraine (The Target Study)*, Headache (Sep. 8, 2014).

S.J. Tepper et al., *AVP-825 Breath-Powdered Intranasal Delivery System Containing 22 mg Sumatriptan Powder vs. 100 mg Oral Sumatripta in the Acute Treatment of Migraines (The Compass Study): A Comparative Randomized Clinical Trial Across Multiple Attacks*, Headache: The Journal of Head and Face Pain (Mar. 29, 2015).

D. S. Quintana et al., *Low-dose Oxytocin Delivered Intranasally with Breath Powdered Device Affects Social-Cognitive Behavior: A Randomized Four-Way Crossover Trial with Nasal Cavity Dimension Assessment*, Transl Psychiatry (Jul. 14, 2015).

R. Mahmoud, *Breathe Out*, Innovations in Phar, Tech. (Dec. 10, 2015).

Chen et al., *Intranasal absorption of rizatriptan—in vivo pharmacokinetics and bioavailability study in humans*, 60 Pharmazie 39-41 (Jan. 2005).

Wang et al., *Uptake and biodistribution of rizatriptan to blood and brain following different routes of administration in rats*, 337 Int J Pharm 155-160 (2007).

\* cited by examiner

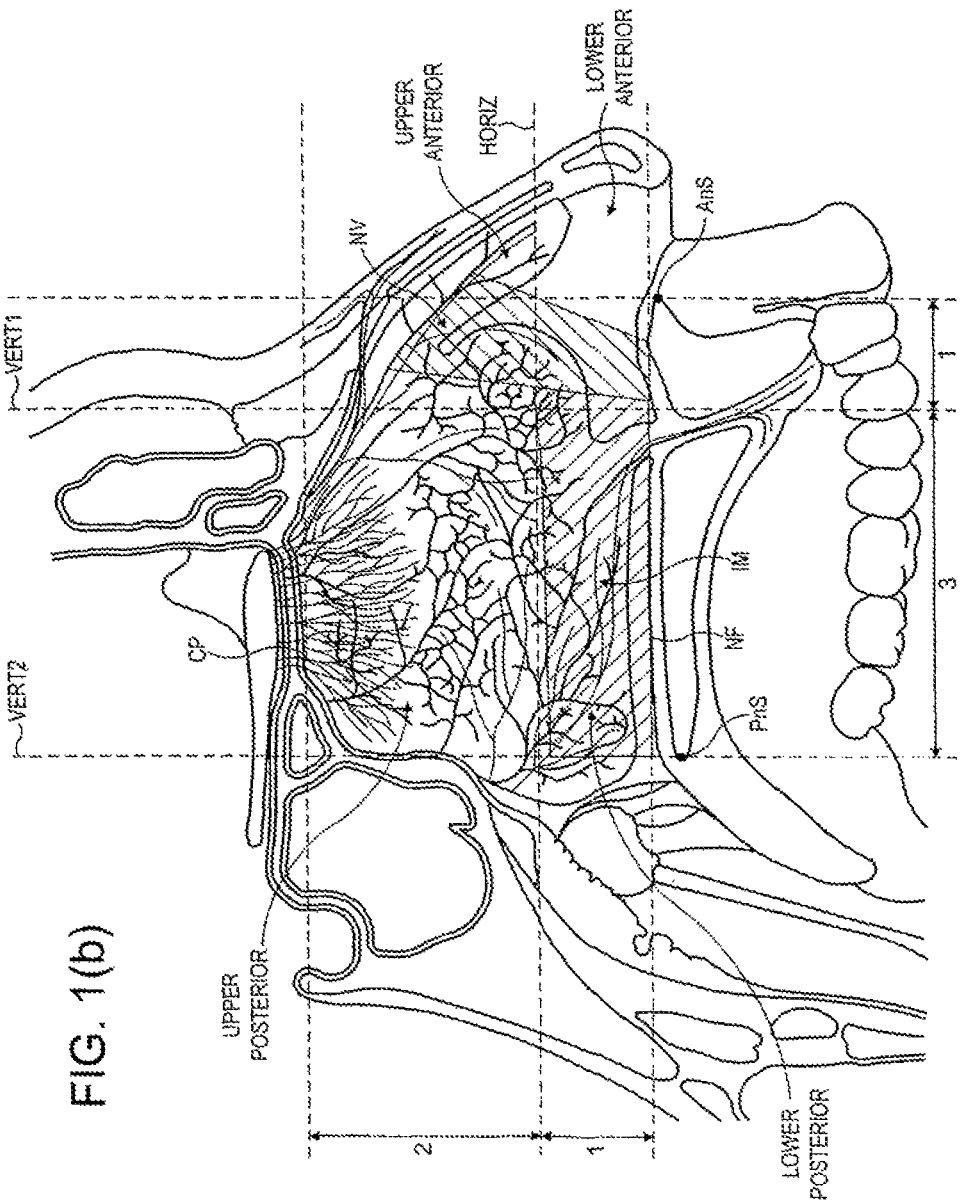

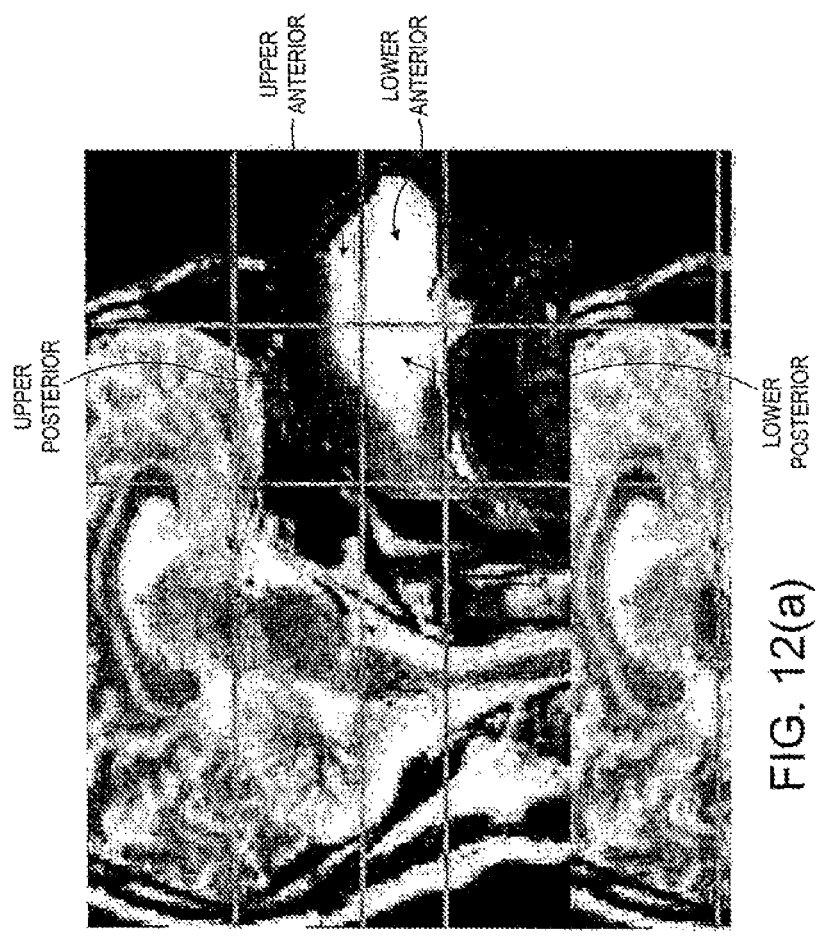

NASAL ADMINISTRATION

The present invention relates to the nasal administration of substances, in particular drugs, to the central nervous system (CNS) via the nasal airway.

Referring to FIG. 1(a), the nasal airway 1 comprises the two nasal cavities separated by the nasal septum, which airway 1 includes numerous ostia, such as the paranasal sinus ostia 3 and the tubal ostia 5, and olfactory cells, and is lined by the nasal mucosa. The nasal airway 1 can communicate with the nasopharynx 7, the oral cavity 9 and the lower airway 11, with the nasal airway 1 being in selective communication with the anterior region of the nasopharynx 7 and the oral cavity 9 by opening and closing of the oropharyngeal velum 13. The velum 13, which is often referred to as the soft palate, is illustrated in solid line in the closed position, as achieved by providing a certain positive pressure in the oral cavity 9, such as achieved on exhalation through the oral cavity 9, and in dashed line in the open position.

In existing administration systems which provide for the administration of drugs to the CNS, which include pulmonary, parenteral, transdermal and oral administration systems, the concentration of drug that is attained within the CNS is mediated by the blood plasma concentration in the systemic, peripheral circulation. For many drugs, the concentration attainable within the CNS is much less than 10% of the blood plasma concentration.

Consequently, high blood plasma concentrations are required in order to achieve effective concentrations in the CNS. However, high blood plasma concentrations can cause unwanted effects, notably, systemic side effects. Thus, it is necessary to provide for a balance of the CNS efficacy against the peripheral side effect.

This may be particularly problematic in systems which require a rapid onset of action, as such systems rely on achieving high blood plasma concentrations in order to create a significant driving gradient for the rapid uptake of drug into the CNS.

Examples of drugs which exhibit systemic side effects include dopamine agonists, such as apomorphine and its derivatives and analogues, which can cause nausea as a side effect, triptans, such as sumatriptan and its derivatives and analogues, which can cause an angina-like side effect, vasopressin and desmopressin analogues which have activity on the learning pathway and can cause enuresis as a side effect, acetylcholinesterase inhibitors which can cause gastro-intestinal (GI) disorders as a side effect, and insulin which exhibits a reduced blood glucose level as a side effect.

It is one aim of the present invention to provide for the administration of substances, in particular drugs, at greater concentrations to the CNS for the same or reduced blood plasma concentrations, which has the benefit of at least reducing any peripheral side effects, which may be undesired. Such administration has particular benefit in relation to rescue situations.

It is another aim of the present invention to achieve a faster onset of action as compared to at least ones of the existing administration systems, and in particular existing nasal spray administration systems.

It is a further aim of the present invention to achieve a relatively rapid onset of action, but where avoiding the sharp peak plasma profiles associated with existing administration systems, such as in pulmonary, intravenous and transdermal systems.

The present inventors have recognized that an increased delivery of substance to the posterior region of the nasal airway, and in particular the upper posterior region of the nasal airway, as illustrated in FIG. 1(b), relative to the anterior region of the nasal airway, surprisingly provides for a disproportionately greater CNS effect, which is suggestive of a greater uptake of substance into the CNS than would be predicted from the blood plasma concentration of the substance.

The posterior region of the nasal airway is that region which is posterior of the nasal valve NV, as illustrated in FIG. 1(b). The nasal valve comprises the anterior bony cavum which contains inferior turbinate erectile tissue and septal erectile tissue, which are supported respectively by compliant ala tissue and the rigid cartilaginous septum (Mosby). These elements combine to form a dynamic valve, which extends over several millimetres, that adjusts nasal airflow, and is stabilized by cartilage and bone, modulated by voluntary muscle and regulated by erectile tissue. The lumen of the nasal valve is the section of narrowest cross-sectional area between the posterior and anterior regions of the nasal airway, and is much longer and narrower dorsally than ventrally, and this lumen defines a triangular entrance which extends to the piriform region of the bony cavum. The nasal valve is lined in its anterior part with transitional epithelium, with a gradual transition posterior to respiratory epithelium. The nasal valve and anterior vestibule define roughly the anterior one-third of the nose.

The posterior region of the nasal airway is that region which is lined with respiratory epithelium, which is ciliated, and olfactory epithelium, which comprises nerves which extend downwards through the cribiform plate CP from the olfactory bulb, whereas the anterior region of the nasal airway is that region which is lined with squamous epithelium, which is not ciliated, and transitional epithelium. The olfactory epithelium extends on both the lateral and medial sides of the nasal airway, and typically extends downwards about 1.5 to 2.5 cm.

The upper posterior region is the region above the inferior meatus IM, as illustrated in FIG. 1(b), and encompasses the middle turbinate, the sinus ostia in infundibulum (ostia to maxillary, frontal and ethmoidal sinuses), the olfactory region, and the upper branches of the trigeminal nerve, and is that region which includes veins which drain to the venous sinuses that surround the brain.

As illustrated in FIG. 1(b), the posterior region of the nasal airway is the nasal region posterior of an imaginary vertical plane VERT1 which is located at a position corresponding to one-quarter of the distance between the anterior nasal spine AnS, which is a pointed projection at the anterior extremity of the intermaxillary suture, and the posterior nasal spine PnS, which is the sharp posterior extremity of the nasal crest of the hard palate and represents the transition between the nose and the nasopharynx, which corresponds to a distance posterior of the anterior nasal spine AnS of between about 13 mm and about 14 mm (Rosenberger defines the distance between the anterior nasal spine AnS and the posterior nasal spine PnS as being 56 mm in eighteen year old boys and 53.3 mm in eighteen year old girls). As again illustrated in FIG. 1(b), the posterior nasal region is bounded posteriorly by an imaginary vertical plane VERT2 which extends through the posterior nasal spine PnS.

As further illustrated in FIG. 1(b), the upper region of the nasal airway is an upper segment of the nasal airway which is bounded by the cribiform plate CP and a horizontal plane HORIZ which is located at a position corresponding to one-third of the distance between the nasal floor NF of the nasal airway and the cribiform plate CP, which corresponds to a height of typically between about 13 and about 19 mm above the nasal floor NF (Zacharek et al define the distance from the nasal floor NF to the cribiform plate CP as 46+/−4 mm).

The upper posterior region is thus that upper posterior region which is bounded by the above-defined vertical and horizontal planes VERT1, HORIZ.

The present inventors have postulated that this increased concentration within the CNS arises as a result of the veins in the upper posterior region of the nasal airway draining backwards to the venous sinuses that surround the brain, which leads to a higher local concentration in the cerebrovasculature. Although the sinus cavernous is outside the blood-to-brain barrier, animal models have shown that substances can be transported by a counter-current mechanism from the veins therein to the carotid artery which passes through the sinus cavernous. Other mechanisms have been proposed which include extra axonal transport along the surface of the olfactory and trigeminal nerves. This mode of transport is apparently quite rapid as compared to intra axonal transport.

The improved efficacy as achieved by the present invention as compared to existing nasal spray administration systems can apparently be explained in that such nasal spray administration systems have been determined to deliver largely to the anterior one-third of the nasal airway, that is, the nasal region anterior of the nasal valve, from which region drainage is mainly along the floor of the nose and in which region the veins drain to the external facial vein, which in turn drains to the external carotid and in turn to the peripheral circulation.

Recently, there has been a growing interest in alternative forms of drug administration, and in particular nasal administration. Nasal administration, with transmucosal absorption, can offer advantages, such as ease of . administration, rapid onset and patient control. Also, in bypassing gastrointestinal and hepatic pre-systemic elimination, nasal administration is applicable in nauseated and vomiting patients who may have problems in taking oral medication.

Several techniques and devices for intranasal drug administration have been developed. However, the use of manually-actuated spray pumps still dominates.

The present applicant has developed a novel nasal delivery system, as disclosed in WO-A-2000/051672, the content of which is herein incorporated by reference, which provides for the delivery of drugs and vaccines in a bi-directional air flow through the two nasal passages when connected in series by closure of the oropharyngeal velum.

In one embodiment this delivery system includes a mouthpiece through which the subject exhales, a nosepiece which is in fluid communication with the mouthpiece, and a spray pump which is actuated in response to exhalation through the mouthpiece to deliver an aerosol spray containing a substance from the nosepiece, such that an aerosol spray is delivered from the nosepiece together with an air flow which acts to entrain the delivered aerosol spray. In exhaling through the mouthpiece, the oropharyngeal velum closes the communication between the oral and nasal cavities to establish a bi-directional air flow which enters one nostril and exits the other nostril.

In one aspect the present invention provides a delivery device for providing for delivery of substance to the central nervous system (CNS) of a subject, the delivery device comprising: a nosepiece unit for insertion into a nasal cavity of a subject and comprising an outlet unit which includes a nozzle for delivering substance into the nasal cavity of the subject; and a substance supply unit which is operable to deliver a dose of substance to the nozzle; wherein the delivery device is configured such that at least 30% of the dose as initially deposited in the nasal cavity is deposited in an upper posterior region of the nasal cavity which is posterior of the nasal valve and above the inferior meatus, thereby providing a CNS concentration of the substance, and hence CNS effect, which is significantly greater than that which would be predicted from a counterpart blood plasma concentration of the substance.

In one embodiment the nozzle is configured to deliver an aerosol spray.

In one embodiment the aerosol spray is a liquid aerosol.

In another embodiment the aerosol spray is a powder aerosol.

In another embodiment the nozzle is configured to deliver a liquid jet.

In a further embodiment the nozzle is configured to deliver a powder jet.

In one embodiment the delivery device further comprises: a mouthpiece through which the subject in use exhales to cause closure of the oropharyngeal velum of the subject.

In one embodiment the outlet unit further comprises a delivery channel which is fluidly connected to the mouthpiece, whereby exhaled air from an exhalation breath of the subject is delivered through the nosepiece unit into the nasal cavity of the subject.

In another embodiment the outlet unit further comprises a delivery channel through which a gas flow, separate to an exhaled air flow from an exhalation breath of the subject, is in use delivered to the nasal cavity of the subject, and the delivery device further comprises: a gas supply unit for supplying a gas flow to the delivery channel.

In one embodiment the substance supply unit is breath actuated.

In another embodiment the substance supply unit is manually actuated.

Preferably, the delivery device is configured such that at least 40% of the dose as initially deposited in the nasal cavity is deposited in the upper posterior region of the nasal cavity.

More preferably, the delivery device is configured such that at least 50% of the dose as initially deposited in the nasal cavity is deposited in the upper posterior region of the nasal cavity.

In one embodiment the outlet unit further comprises a cuff member which acts to obstruct a region of the nasal cavity which is anterior of the nasal valve, such that substantially all of the delivered dose is delivered to a region of the nasal cavity which is posterior of the nasal valve.

In one embodiment the cuff member acts to close the nasal valve.

In another embodiment the outlet unit includes no cuff member which obstructs a region of the nasal cavity which is anterior of the nasal valve.

In one embodiment the region posterior of the nasal valve represents the posterior two-thirds of the nasal cavity and the region anterior of the nasal valve represents the anterior one-third of the nasal cavity.

In one embodiment the ratio of the peak CNS effect to the peak blood plasma concentration is at least 2 times that achieved using intravenous (IV) delivery.

Preferably, the ratio of the peak CNS effect to the peak blood plasma concentration is at least 3 times that achieved using intravenous (IV) delivery.

In another aspect the present invention provides a method of delivering substance to the central nervous system (CNS) of a subject, the method comprising the steps of: inserting a nosepiece unit into a nasal cavity of a subject, wherein the nosepiece unit comprises an outlet unit which includes a nozzle for delivering substance into the nasal cavity of the subject; and delivering a dose of substance to the nozzle; wherein at least 30% of the dose as initially deposited in the nasal cavity is deposited in an upper posterior region of the nasal airway which is posterior of the nasal valve and above the inferior meatus, thereby providing a CNS concentration of the substance, and hence CNS effect, which is significantly greater than that which would be predicted from a counterpart blood plasma concentration of the substance.

In one embodiment the nozzle is configured to deliver an aerosol spray.

In one embodiment the aerosol spray is a liquid aerosol.

In another embodiment the aerosol spray is a powder aerosol.

In another embodiment the nozzle is configured to deliver a liquid jet.

In a further embodiment the nozzle is configured to deliver a powder jet.

In one embodiment the method further comprises the step of: the subject exhaling through a mouthpiece to cause closure of the oropharyngeal velum of the subject.

In one embodiment the outlet unit is fluidly connected to the mouthpiece, whereby exhaled air from an exhalation breath of the subject is delivered through the nosepiece unit into the nasal cavity of the subject, such as to entrain the delivered substance.

In another embodiment a gas flow, separate to an exhaled air flow from an exhalation breath of the subject, is delivered to the nasal cavity of the subject, such as to entrain the delivered substance.

In one embodiment a dose of the substance is delivered in response to exhalation by the subject.

In another embodiment a dose of the substance is delivered in response to a manual operation by the subject.

Preferably, at least 40% of the dose as initially deposited in the nasal cavity is deposited in the upper posterior region of the nasal cavity.

More preferably, at least 50% of the dose as initially deposited in the nasal cavity is deposited in the upper posterior region of the nasal cavity.

In one embodiment the method further comprises the step of: obstructing a region of the nasal cavity which is anterior of the nasal valve, such that substantially all of the delivered dose is delivered to a region of the nasal cavity which is posterior of the nasal valve.

In one embodiment the obstructing step comprises the step of: closing the nasal valve.

In another embodiment a fluid communication remains between a region of the nasal cavity which is anterior of the nasal valve and a region of the nasal cavity which is posterior of the nasal valve.

In one embodiment the region posterior of the nasal valve represents the posterior two-thirds of the nasal cavity and the region anterior of the nasal valve represents the anterior one-third of the nasal cavity.

In one embodiment the ratio of the peak CNS effect to the peak blood plasma concentration is at least 2 times that achieved using intravenous (IV) delivery.

Preferably, the ratio of the peak CNS effect to the peak blood plasma concentration is at least 3 times that achieved using intravenous (IV) delivery.

In one embodiment the substance is a pharmaceutical drug.

In one embodiment the substance exhibits one or more systemic side effects.

In one embodiment the substance is a dopamine agonist.

Preferably, the substance comprises apomorphine or its pharmaceutically-acceptable derivatives or analogues.

In another embodiment the substance is a triptan.

Preferably, the substance comprises sumatriptan or its pharmaceutically-acceptable derivatives or analogues.

In a further embodiment the substance has activity on the learning pathway.

In one embodiment the substance comprises vasopressin or its pharmaceutically-acceptable derivatives or analogues.

In another embodiment the substance comprises desmopressin or its pharmaceutically-acceptable derivatives or analogues.

In a still further embodiment the substance is an acetylcholinesterase inhibitor.

Preferably, the substance comprises rivastigmine or its pharmaceutically-acceptable derivatives or analogues.

In one embodiment the substance is for the treatment of a condition which requires a rapid onset of action in order to ameliorate or abort a CNS event.

In one embodiment the substance is a benzodiazepine for the treatment of a panic disorder.

In another embodiment the substance is a triptan for the treatment of migraine.

In a further embodiment the substance is a gaba agonist for the treatment of neuropathic pain or to abort a partial or full epilepsy seizure.

In a still further embodiment the substance is insulin which is administered to regulate the satiety center.

In a yet further embodiment the substance is an insulin-like growth factor or its pharmaceutically-acceptable analogues which is administered to regulate the satiety center.

In yet another embodiment the substance is a peptide which is administered to regulate the satiety center.

In a still yet further embodiment the substance is a memory-enhancing agent which is administered prior to a learning episode.

In still yet another embodiment the substance is a sedative.

In one embodiment the substance is for the treatment of a panic disorder.

In another embodiment the substance is for the treatment of migraine.

In a further embodiment the substance is for the treatment of neuropathic pain.

In a still further embodiment the substance is for aborting a partial or full epilepsy seizure.

In yet another embodiment the substance is for regulating the satiety center.

In still yet another embodiment the substance is a memory-enhancing agent which is administered prior to a learning episode.

In a yet further embodiment the substance is for the treatment of a neurological disease, such as multiple sclerosis (MS), Alzheimer's disease or Parkinson's disease.

In still another embodiment the substance is for the treatment of sexual dysfunction.

In yet another embodiment the substance is a therapeutic vaccine, such as for the treatment of intracerebral tumours.

In a still further embodiment the substance is an angiotensin-converting enzyme (ACE) inhibitor, such as for the treatment of hypertension.

In a yet further embodiment the substance is for the treatment of insomnia.

In one embodiment the substance is a benzodiazepine.

In another embodiment the substance is a substance which acts on benzodiazepine receptors.

In a still further embodiment the substance is for the treatment of depression.

In one embodiment the substance is a selective serotonin re-uptake inhibitor.

In another embodiment the substance is a tricyclic anti-depressant.

In a yet further embodiment the substance is for the treatment of agrophobia.

In still another embodiment the substance is for the treatment of social anxiety disorder.

In still yet another embodiment the substance is for the treatment of obsessive compulsive disorder.

In yet still another embodiment the substance is for use in a treatment of smoking cessation.

In one embodiment the substance comprises nicotine.

In a still further embodiment the substance is a selective serotonin re-uptake inhibitor.

The present invention will now be described hereinbelow by way of example only with reference to the accompanying drawings, in which:

FIG. 1(a) schematically illustrates the anatomy of the upper respiratory tract of a human subject;

FIG. 12(a) illustrates the cumulative deposition as obtained by the conventional nasal spray administration system as employed in Example #2;

Figure 1A:
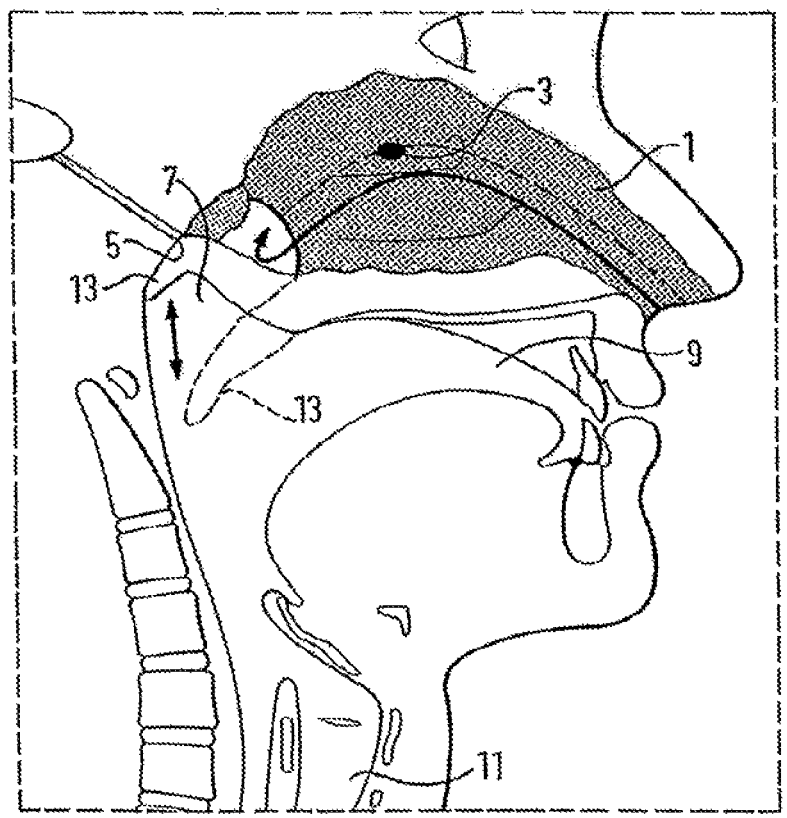
FIG. 1(b) illustrates the segmentation of a nasal cavity in accordance with a preferred embodiment of the present invention.
Figure 2:
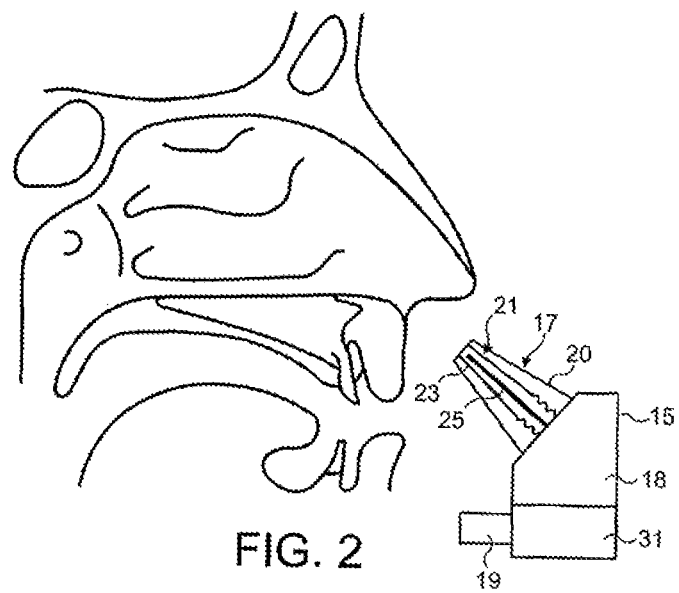
FIG. 2 illustrates a nasal delivery device in accordance with a first embodiment of the present invention.
Figure 13:
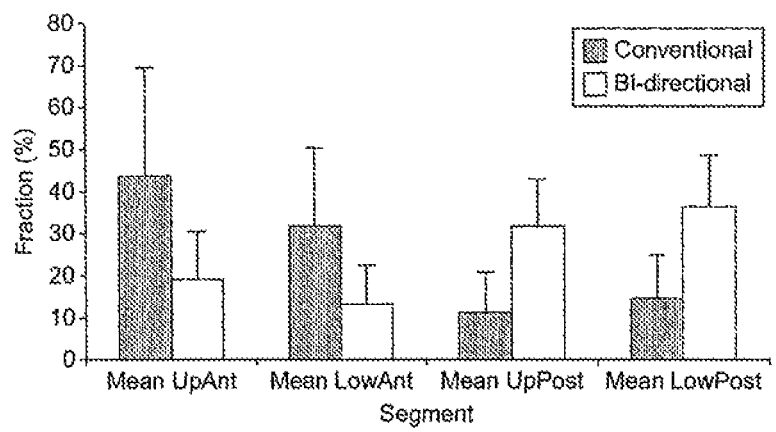
Figure 14:
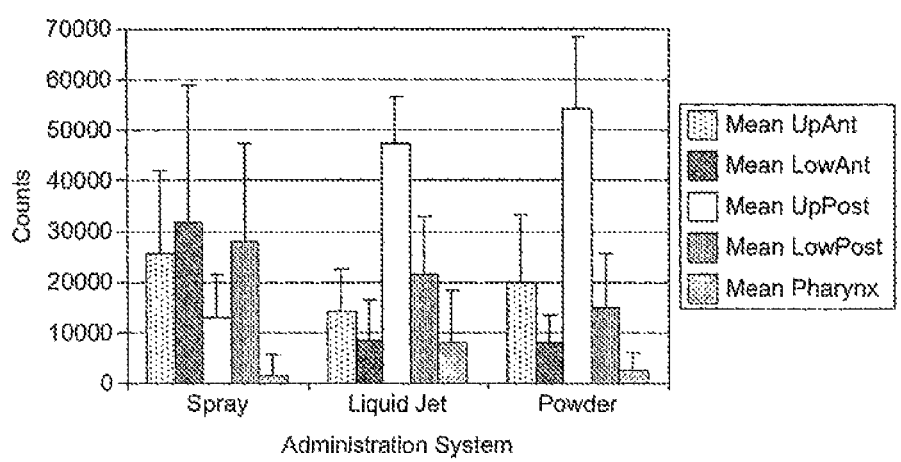
Figure 15:
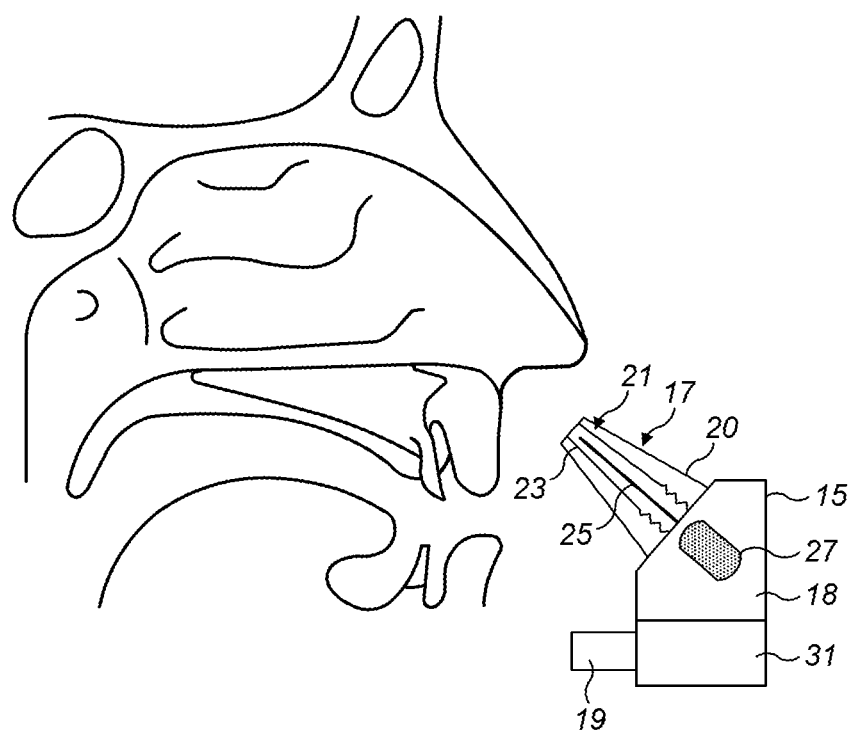

FIG. 13 graphically illustrates the mean deposition fractions in the four segmented nasal regions for both the conventional nasal spray administration system and the bi-directional administration system as employed in Example #2;

FIG. 14 graphically illustrates the mean deposition fractions in the four segmented nasal regions for both the conventional nasal spray administration system and the bi-directional administration systems as employed in Example #3; and FIG. 15 illustrates the nasal delivery device of FIG. 2 where providing for delivery of substance from a capsule.

Figure 3:
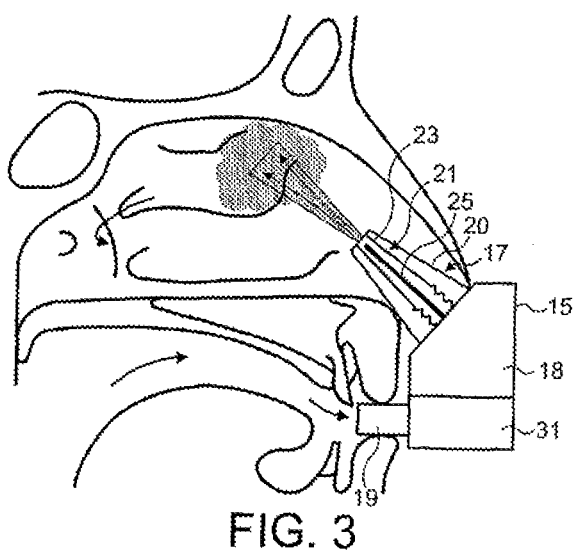
FIG. 3 illustrates the nasal delivery device of FIG. 2, where operative in delivering substance to the nasal cavity of the subject.
Figure 4:
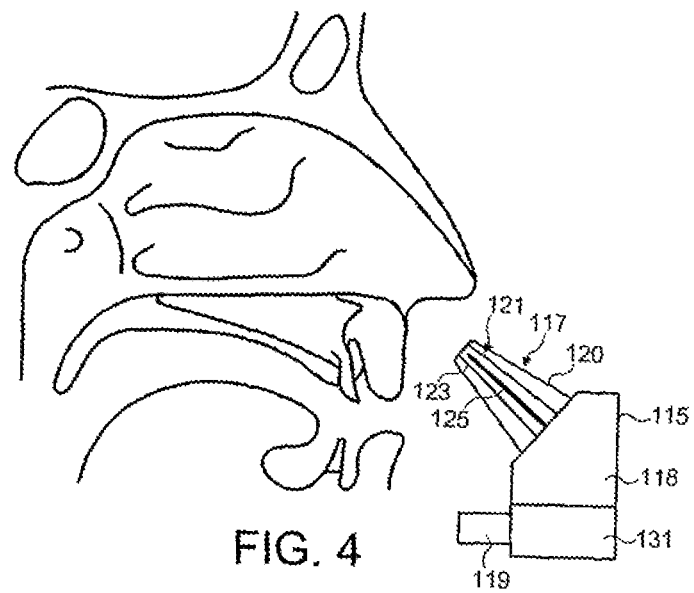
FIG. 4 illustrates a nasal delivery device in accordance with a second embodiment of the present invention.

FIGS. 2 and 3 illustrate a nasal delivery device in accordance with a first embodiment of the present invention.

The delivery device comprises a housing 15, a nosepiece unit 17 for fitting in a nasal passage of a subject, a substance supply unit 18 for delivering substance to the nosepiece unit 17, and a mouthpiece 19 through which the subject exhales to actuate the delivery device.

The nosepiece unit 17 comprises a nosepiece 20, in this embodiment a frusto-conical element, for guiding the nosepiece unit 17 into a nasal passage of the subject and providing a fluid-tight seal with the nares of the nostril, and an outlet unit 21 for delivering substance, in this embodiment a CNS-active drug, to an upper posterior region of the nasal passage of the subject, in this embodiment an upper posterior region as bounded by a vertical plane which is located posterior of the anterior nasal spine AnS at a position corresponding to one-quarter of the distance between the anterior and posterior nasal spines AnS, PnS and a horizontal plane which is located above the nasal floor at a height one-third of the distance between the nasal floor and the cribiform plate. As discussed hereinabove, the present inventors have recognized that an increased delivery of substance to the upper posterior region of the nasal passage surprisingly provides for a disproportionately greater uptake of substance into the CNS than would be predicted from the blood plasma concentration of the substance.

In this embodiment the outlet unit 21 comprises a delivery channel 23 which is in fluid communication with the mouthpiece 19 such that an air flow is delivered into and through the nasal airway of the subject on exhalation by the subject through the mouthpiece 19, and a nozzle 25 which is in fluid communication with the substance supply unit 18 and provides for delivery of substance into the nasal passage of the subject.

In this embodiment the substance supply unit 18 comprises a mechanical delivery pump, in particular a liquid delivery pump or a powder delivery pump, which delivers metered doses of substance, on actuation thereof.

In another alternative embodiment the substance supply unit 18 could comprise a dry powder delivery unit which delivers metered doses of a substance, as a dry powder, on actuation thereof. In one embodiment the substance supply unit 18 could provide for delivery of substance from a capsule.

In yet another alternative embodiment the substance supply unit 18 could comprise an aerosol canister which delivers metered volumes of a propellant, preferably a hydrofluoroalkane (HFA) propellant or the like, containing substance, either as a suspension or solution.

In yet another alternative embodiment the substance supply unit 18 could comprise a nebulizer which delivers metered doses of a substance, as an aerosol spray, on actuation thereof.

In this embodiment the nozzle 25 is configured to deliver a significant fraction of substance to the upper posterior region of the nasal passage, here an initial deposition of greater than 30% of the delivered dose.

In this embodiment the nozzle 25 is configured to deliver substance as an aerosol spray.

In an alternative embodiment the nozzle 25 could be configured to deliver substance as a jet, for example, as a column of liquid or powder. In delivering the substance as a jet, the substance can be more readily targeted at the upper posterior region of the nasal passage.

In this embodiment the substance supply unit 18 is a multi-dose unit for delivering a plurality of metered doses of the substance. In another embodiment the substance supply unit 18 could be a single-dose unit for delivering a single metered dose of the substance.

The substance supply unit 18 is pre-primeable, in this embodiment by loading a resilient element, and includes a breath-actuated release mechanism 31 which, when triggered, releases the resilient element and actuates the substance supply unit 18 to deliver a metered dose of the substance through the nozzle 25.

In this embodiment the trigger mechanism 31 is configured to cause actuation of the substance supply unit 18 on generation of a predetermined pressure at the delivery channel 23.

In an alternative embodiment the trigger mechanism 31 could be configured to cause actuation of the substance supply unit 18 on generation of a predetermined flow rate through the delivery channel 23.

Operation of the delivery device will now be described hereinbelow with reference to FIG. 3 of the accompanying drawings.

The nosepiece unit 17 is first inserted into one of the nasal passages of a subject until the nosepiece 20 abuts the nares of the nostril such as to establish a fluid-tight seal therewith, at which point the distal end of the outlet unit 21 extends about 2 cm into the nasal passage of the subject, and the mouthpiece 19 is gripped in the lips of the subject.

The subject then begins to exhale through the mouthpiece 19, which exhalation acts to close the oropharyngeal velum of the subject and drive an air flow through the delivery channel 23 of the outlet unit 21, with the air flow passing into the one nasal passage, around the posterior margin of the nasal septum and out of the other nasal passage, thereby achieving a bi-directional air flow through the nasal airway of the subject.

In this embodiment, when the pressure developed at the delivery channel 23 reaches a predetermined value, the release mechanism 31 is triggered to actuate the substance supply unit 18 to deliver a metered dose of the substance to the nozzle 25 and into the nasal passage of the subject.

In an alternative embodiment the release mechanism 31 could be triggered in response to the generation of a predetermined flow rate through the delivery channel 23.

In this embodiment, where the delivery device is a multi-dose device, the device is ready for further use following priming of the substance supply unit 18.

FIGS. 4 and 5 illustrate a nasal delivery device in accordance with a second embodiment of the present invention.

The delivery device comprises a housing 115, a nosepiece unit 117 for fitting in a nasal passage of a subject, a substance supply unit 118 for delivering substance to the nosepiece unit 117, and a mouthpiece 119 through which the subject exhales to actuate the delivery device.

The nosepiece unit 117 comprises a nosepiece 120, in this embodiment a frusto-conical element, for guiding the nosepiece unit 117 into a nasal passage of the subject and being configured both to provide a fluid-tight seal with the nares of the nostril and obstruct, in this embodiment close, the nasal passage at a position therealong, in this embodiment at a position corresponding substantially to the nasal valve, thereby obstructing the anterior one-third of the nasal passage and leaving open the posterior two-thirds of the nasal passage, as illustrated in FIG. 5, and an outlet unit 121 for delivering substance, in this embodiment a CNS-active drug, to an upper posterior region of the nasal passage of the subject, in this embodiment an upper posterior region as bounded by a vertical plane which is located posterior of the anterior nasal spine AnS at a position corresponding to one-quarter of the distance between the anterior and posterior nasal spines AnS, PnS and a horizontal plane which is located above the nasal floor at a height one-third of the distance between the nasal floor and the cribiform plate. As discussed hereinabove, the present inventors have recognized that an increased delivery of substance to the upper posterior region of the nasal passage surprisingly provides for a disproportionately greater uptake of substance into the CNS than would be predicted from the blood plasma concentration of the substance.

In this embodiment the outlet unit 121 comprises a delivery channel 123 which is in fluid communication with the mouthpiece 119 such that an air flow is delivered into and through the nasal airway of the subject on exhalation by the subject through the mouthpiece 119, and a nozzle 125 which is in fluid communication with the substance supply unit 118 and provides for delivery of substance into the nasal passage of the subject.

In this embodiment the nosepiece 120 is formed of a substantially rigid material, but in other embodiments could be formed of a soft compressible and/or flexible material.

In this embodiment the substance supply unit 118 comprises a mechanical delivery pump, in particular a liquid delivery pump or a powder delivery pump, which delivers metered doses of substance, on actuation thereof.

In another alternative embodiment the substance supply unit 118 could comprise a dry powder delivery unit which delivers metered doses of substance, as a dry powder, on actuation thereof. In one embodiment the substance supply unit 118 could provide for delivery of substance from a capsule.

In yet another alternative embodiment the substance supply unit 118 could comprise an aerosol canister which delivers metered volumes of a propellant, preferably a hydrofluoroalkane (HFA) propellant or the like, containing substance, either as a suspension or solution.

In yet another alternative embodiment the substance supply unit 118 could comprise a nebulizer which delivers metered doses of substance, as an aerosol spray, on actuation thereof.

In this embodiment the nozzle 125 is configured to deliver substance as an aerosol spray.

In an alternative embodiment the nozzle 125 could be configured to deliver substance as a jet, for example, as a column of liquid or powder. In delivering the substance as a jet, the substance can be more readily targeted at the posterior region of the nasal passage.

In this embodiment the substance supply unit 118 is a multi-dose unit for delivering a plurality of metered doses of the substance. In another embodiment the substance supply unit 118 could be a single-dose unit for delivering a single metered dose of the substance.

The substance supply unit 118 is pre-primeable, in this embodiment by loading a resilient element, and includes a breath-actuated release mechanism 131 which, when triggered, releases the resilient element and actuates the substance supply unit 118 to deliver a metered dose of the substance through the nozzle 125.

In this embodiment the trigger mechanism 131 is configured to cause actuation of the substance supply unit 118 on generation of a predetermined pressure at the delivery channel 123.

In an alternative embodiment the trigger mechanism 131 could be configured to cause actuation of the substance supply unit 118 on generation of a predetermined flow rate through the delivery channel 123.

Figure 5:
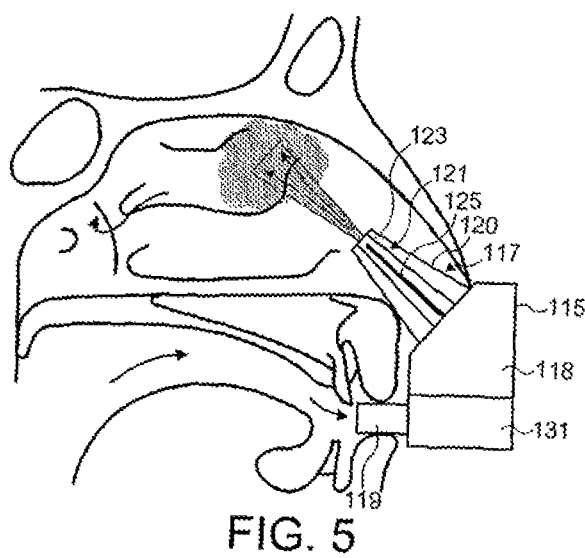
FIG. 5 illustrates the nasal delivery device of FIG. 4, where operative in delivering substance to the nasal cavity of the subject.

Operation of the delivery device will now be described hereinbelow with reference to FIG. 5 of the accompanying drawings.

The nosepiece unit 117 is first inserted into one of the nasal passages of a subject until the nosepiece 120 abuts the nares of the nostril such as to establish a fluid-tight seal therewith, at which point the distal end of the nosepiece 120 extends about 2 cm into the nasal passage of the subject and closes the nasal valve, and the mouthpiece 119 is then gripped in the lips of the subject.

The subject then begins to exhale through the mouthpiece 119, which exhalation acts to close the oropharyngeal velum of the subject and drive an air flow through the delivery channel 123 of the outlet unit 121, with the air flow passing into the one nasal passage, around the posterior margin of the nasal septum and out of the other nasal passage, thereby achieving a bi-directional air flow through the nasal airway of the subject.

In this embodiment, when the pressure developed at the delivery channel 123 reaches a predetermined value, the release mechanism 131 is triggered to actuate the substance supply unit 118 to deliver a metered dose of the substance to the nozzle 125 and into the nasal passage of the subject.

In an alternative embodiment the release mechanism 131 could be triggered in response to the generation of a predetermined flow rate through the delivery channel 123.

In this embodiment, where the delivery device is a multi-dose device, the device is ready for further use following priming of the substance supply unit 118.

Figure 6:
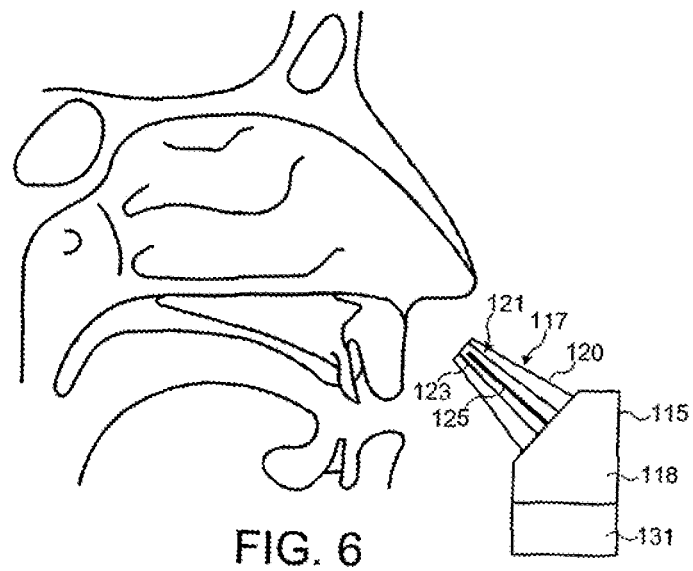
FIG. 6 illustrates a nasal delivery device in accordance with a third embodiment of the present invention.
Figure 7:
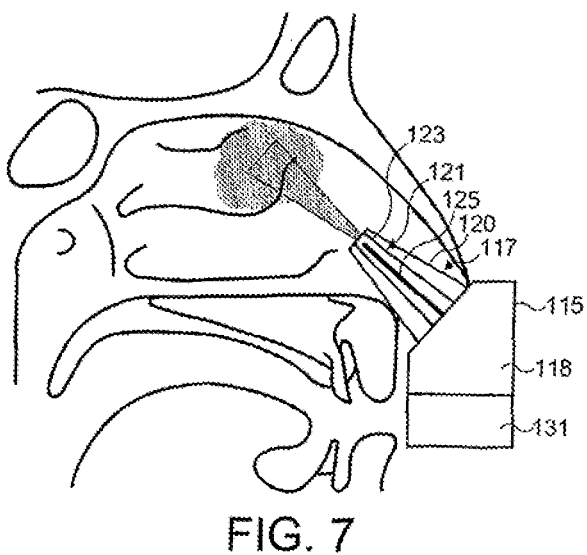
FIG. 7 illustrates the nasal delivery device of FIG. 6, where operative in delivering substance to the nasal cavity of the subject.

FIGS. 6 and 7 illustrate a nasal delivery device in accordance with a third embodiment of the present invention.

The delivery device of this embodiment is very similar to the delivery device of the above-described second embodiment, and thus, in order to avoid unnecessary duplication of description, only the differences will be described in detail, with like reference signs designating like parts.

The delivery device of this embodiment differs from that of the above-described second embodiment in omitting the mouthpiece 119 and the release mechanism 131 being manually actuated.

Operation of this delivery device is similar to that of the above-described second embodiment, except in that a bi-directional air flow is not generated through the nasal airway and the release mechanism 131 is actuated manually by the subject.

The present invention will now be described hereinbelow with reference to the following non-limiting Examples.

EXAMPLE #1

The purpose of this study was to determine the relative sedative effect of midazolam where intranasally delivered using the novel, bi-directional administration system of the present applicant.

In this study, twelve healthy subjects, 4 male and 8 female, were studied.

In separate sessions, the subjects received 3.4 mg of midazolam by one of three different administration systems, these being:

(i) an intravenous administration system in which a midazolam formulation was intravenously administered;
(ii) a conventional nasal spray administration system in which a midazolam formulation was conventionally nasally administered using a spray pump as supplied by Ing Erich Pfeiffer GmbH (Radolfsee, Germany) which is specified to generate a liquid spray with a mean particle size of 43 μm, with 100 μl of the formulation being delivered to each nostril; and
(iii) the bi-directional administration system of the first-described embodiment, and incorporating the same spray pump as the conventional nasal spray administration system, in which a midazolam formulation was nasally administered, with 100 μl of the formulation being delivered to each nostril.

Each study session was six hours in duration, and the sessions were separated by at least one week.

The intravenous formulation was a commercial midazolam HCl formulation (1 mg/ml (free base)) as supplied by Alpharma Inc (New Jersey, USA).

The nasal formulation was an aqueous solution containing midazolam base (1.7% w/v), sulfobutylether-β-cyclodextrin sodium salt with a molar substitution of 6.2 (Captisol®) (14% w/v) as supplied by CyDex Inc (Kansas, USA), hydroxypropyl methylcellulose (0.1% w/v), benzalkonium chloride (0.02% w/v), ethylene diaminetetraacetic acid (0.1% w/v) and phosphoric acid (0.73% w/v). The pH of the formulation was adjusted to a pH of between 4.20 and 4.35 with sodium hydroxide.

Venous blood samples, each having a volume of 9 ml, were drawn just prior to administration and at 2, 5, 10, 15, 20, 25, 30, 35, 45, 60, 90, 120, 240 and 360 minutes after administration, in order to allow for a determination of the blood plasma concentration of midazolam.

The blood plasma concentration of midazolam was determined according to Martens et al.

Samples, spiked with diazepam as an internal standard, were alkalised and extracted by toluene containing 0.1% w/v amyl alcohol. The resulting organic phase for each of the samples was then evaporated and the residue for each of the samples was derivatized with TBDMSTFA (/tert/-Butyldimethylsilyl)-N-methyltrifluoroacetamide with 1% w/v tert-butyldimethylsilyllchloride) at 60 °C. After the excess of TBDMSTFA was evaporated, the residue for each of the samples was dissolved in ethyl acetate and analyzed in a gas chromatograph, in this embodiment an HP 5890 gas chromatograph equipped with an HP 5972 mass-spectrometry detector as supplied by Hewlett Packard Inc (USA). The midazolam and diazepam components were quantified by the mass ions 310 and 256, respectively.

Figure 8:
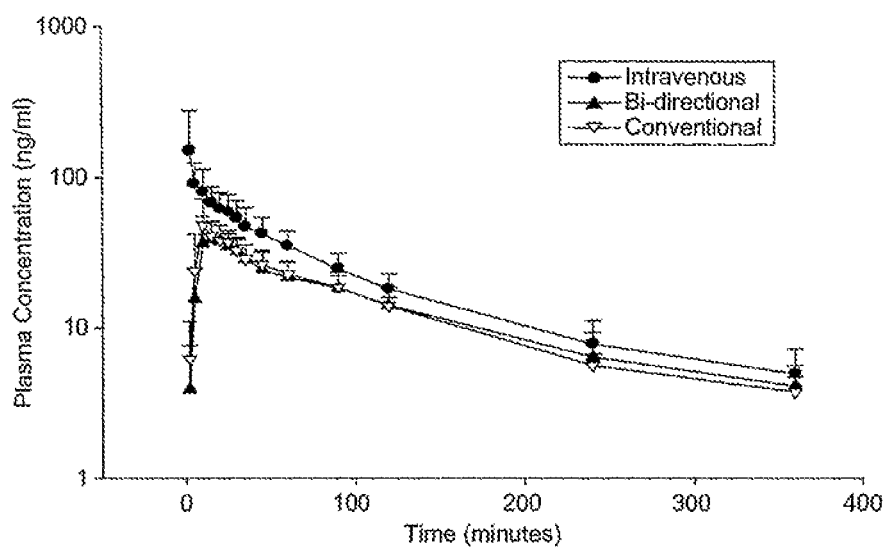
FIG. 8 illustrates the time course for the measured blood plasma concentrations of midazolam for the three exemplified administration systems as employed in Example #1.

FIG. 8 shows the time course for measured blood plasma concentrations of midazolam for the three different administration systems.

The curves for the two nasal administration systems are quite similar, whereas the curve for the intravenous administration system exhibits a blood plasma concentration which is always higher, although it has a parallel time-concentration curve to that of the nasal administration systems. These curves do not seem to be log-linear, indicating that a true elimination phase was not reached within the study session.

Table I below shows the pharmacokinetic characteristics of midazolam for the three administration systems.

In this study, the midazolam clearance, the volume of distribution, the elimination rate, the maximum plasma concentration $C_{max}$, the time maximum plasma concentration $T_{max}$, and the area under the curve AUC (linear trapezoidal rule) were calculated by computerized curve fitting using the Win-Nonlin Standard 4.1 as supplied by Pharsight Corporation (California, USA). The systemic clearance (Cl)=dose/$AUC_{iv}$, the apparent nasal clearances $(Cl_n)$=dose/$AUC_n$, and the respective bioavailabilities $(F_x)$=$(AUC_x$/$dose_x)$/$(AUC_y$/$dose_x)$ were determined from the calculated values.

As can be seen, the two nasal administration systems exhibited similar pharmacokinetics, including a rapid mean $T_{max}$ of 15/16 minutes. The intravenous administration system exhibited a shorter $T_{max}$, and a significantly larger area under the curve AUC. The bio-availabilities for the nasal administration systems were similar, in being 0.68 (037, 0.80) and 0.69 (0.57, 0.81) for the conventional spray administration system and the bi-directional spray administration system, respectively.

the conventional nasal spray administration system, insofar as the bi-directional administration system achieves a substantially greater CNS effect than the conventional nasal spray administration system for a reduced $C_{max}$.

As discussed hereinabove, the present inventors have postulated that this increased concentration within the CNS arises as a result of the veins in the upper posterior region of the nasal passage draining backwards to the venous sinuses that surround the brain, which leads to a higher local concentration in the cerebrovasculature.

EXAMPLE #2

This study provides for characterization of the deposition as achieved by the nasal administration systems of the above-described study.

TABLE I

| Administration System | $T_{max}$ min | $C_{max}$ ng/ml | $T_{1/2}$ min | AUClast min*ng/ml | AUCinf min*ng/ml | Vz #(obs) ml | Cl #(obs) ml/min |
|---|---|---|---|---|---|---|---|
| Intravenous | 2.5 | 152 | 104 | 7349 | 8164 | 65378 | 451 |
|  | 2; 3 | 73; 232 | 87; 121 | 5953; 8744 | 6486; 9842 | 54383; 76373 | 374; 527 |
| Bi-directional | 16 | 44 | 119 | 4615 | 5364 | 98551 | 589 |
|  | 13; 19 | 34; 53 | 98; 139 | 3877; 5354 | 4476; 6252 | 64598; 132504 | 373; 805 |
| Conventional | 15 | 53 | 114 | 4628 | 5267 | 90691 | 551 |
|  | 11; 18 | 39; 66 | 96; 133 | 4211; 5044 | 4792; 5742 | 59419; 12964 | 376; 726 |

The calculations for the conventional nasal spray and bi-directional administration systems are not corrected for bio-availability.

In the results, the data is given as a median (min-max) or a mean (95% confidence interval (CI)). Regression analysis and ANOVA were used as appropriate. A bi-variate correlation (Pearson) was used to determine associations between variables. A paired sample t-test was used for group comparisons.

Subjective sedation was scored by a numeric rating scale (NRS) 0-10, where 0 is fully awake and 10 is falling asleep or as tired as you can imagine at 0, 2, 5, 10, 15, 20, 25, 30, 35, 45, 60, 90, 120 and 360 minutes after administration.

Figure 9:
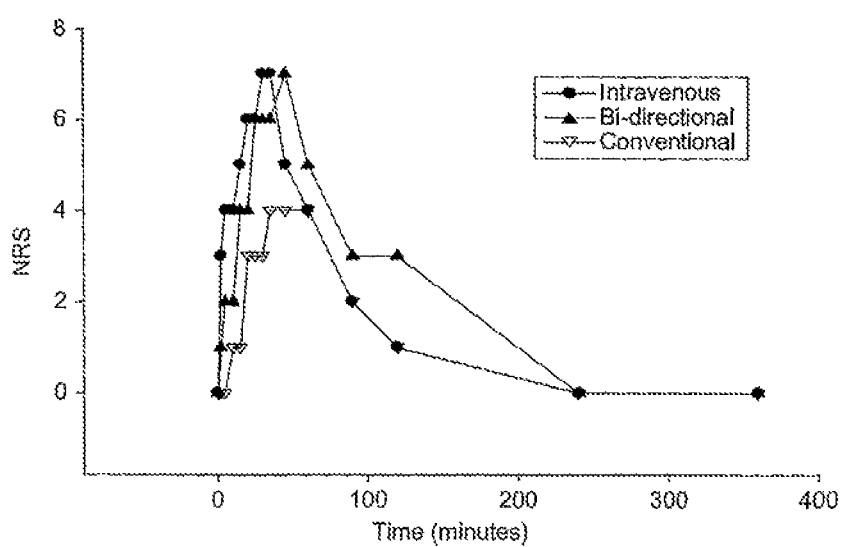
FIG. 9 illustrates the time course for the reported median sedation scores on a numeric rating scale (NRS) following administration of midazolam by the three exemplified administration systems as employed in Example #1.

FIG. 9 represents the time course for subjective reporting of median sedation scores.

As can be seen, the bi-directional administration system achieved sedation scores which were equivalent to those of the intravenous administration system and yet unexpectedly had a much lower $C_{max}$ than that of the intravenous administration system. In addition, the bi-directional administration system has an onset of action which is considerably faster than the conventional nasal spray administration system and almost as fast as the intravenous administration system, and a markedly longer $T_{max}$ than the intravenous administration system.

Figure 10:
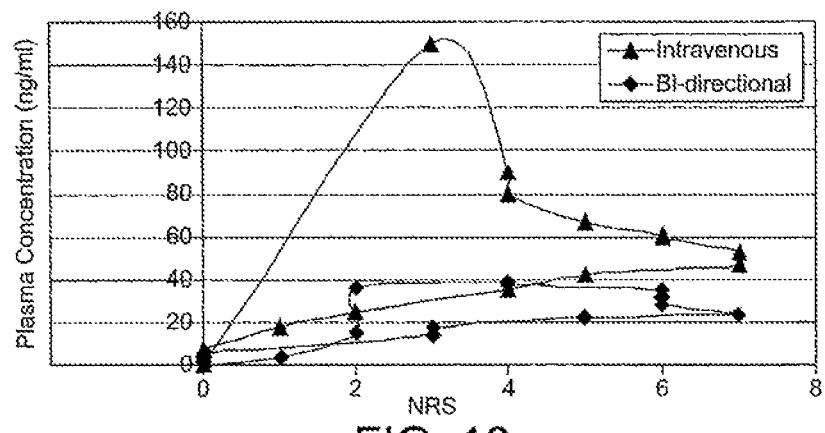
FIG. 10 illustrates a plot of the reported median sedation scores as a function of the measured blood plasma concentration for the intravenous administration system and the bi-directional administration system as employed in Example #1.

FIG. 10 illustrates a plot of the reported median sedation scores as a function of blood plasma concentration for the intravenous administration system and the bi-directional administration system.

This plot clearly illustrates that the bi-directional administration system achieves the same peak CNS effect as the intravenous administration system, but with a substantially lower $C_{max}$. In this embodiment the ratio of peak CNS effect to $C_{max}$ as achieved by the bi-directional administration system is about 3.5 times that achieved by intravenous administration.

Figure 11:
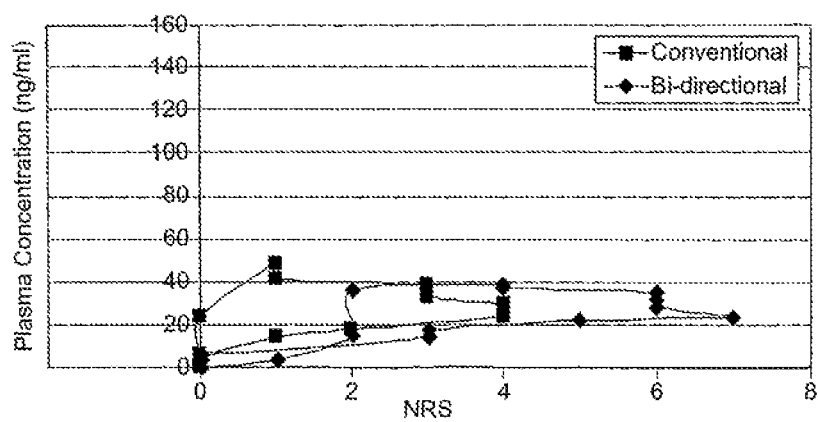
FIG. 11 illustrates a plot of the reported median sedation scores as a function of the measured blood plasma concentration for the bi-directional administration system and the conventional nasal spray administration system as employed in Example #1.

FIG. 11 illustrates a plot of the reported median sedation scores as a function of blood plasma concentration for the bi-directional administration system and the conventional nasal spray administration system.

This plot clearly illustrates the marked effect as achieved by the bi-directional administration system as compared to In this study, nine healthy subjects, 4 females and 5 males, were studied.

In separate sessions, the subjects received a test solution by one of two different nasal administration systems, these corresponding to the nasal administration systems of the above study and being:

(i) a conventional nasal spray administration system in which a labeled test solution was conventionally nasally administered using a spray pump as supplied by Ing Erich Pfeiffer GmbH (Radolfsee, Germany) which is specified to generate a liquid spray with a mean particle size of 43 µm, with 100 µl of the test solution being delivered to one nostril; and (ii) the bi-directional administration system of the first-described embodiment, and incorporating the same spray pump as the conventional nasal spray administration system, in which a labeled test solution was nasally administered, with 100 µl of the test solution being delivered to one nostril.

The two study sessions were performed two days apart to secure complete washout and decay.

The test solution was a $^{99m}$Tc-DTPA solution, which was made by adding 120-150 MBq $^{99m}$TcO$_4^-$ (IFETEC generator) as supplied by Isopharma (Kjeller, Norway) in 6 ml of eluate to a vial containing freeze-dried diethylene triamine pentaacetic acid DTPA as supplied by Isopharma (Kjeller, Norway).

The deposition of the test solution in the nasal cavity was imaged using a scintillation camera system, here a VERTEX camera as supplied by ADAC Laboratories (USA) which was equipped with a low energy parallel hole high resolution VXGP collimator.

The aerosol was administered with the subjects sitting in the upright position, and, following administration, the subjects sat back such that the floor of the nasal cavity was projected at between 30 and 45 degrees with respect to the y-axis of the camera detector. This re-positioning took approximately 1 minute from the dose administration and imaging was initiated immediately thereafter. A total of 16 images, each containing 128×128 pixels, were acquired at two minute intervals. The subjects were instructed not to sniff during the imaging procedure.

As a consequence of the variation in administered activity, the acquired images were normalized so that the first image in each series, which represents the initial deposition, had a total image intensity equal to 100,000 within a region drawn around the nose as appearing in the cumulative images. As the floor of the nose and the curvature of the pharynx were clearly visible in the cumulative images as derived from each of the series, each series of images could conveniently be aligned.

Nasal dimensions were measured by acoustic rhinometry using Rhin2000 anatomic nose adaptors as supplied by RhinoMetrics (Lynge, Denmark), to verify normal nasal dimensions and to assist in nasal segmentation. Acoustic rhinometry identified the location of the minimal cross-sectional area corresponding to the head of the inferior turbinate (mean/SD: 2.3+/−0.25 cm), the head of the middle turbinate (mean/SD: 3.78+/−0.24 cm) and the transition to the epipharynx (mean/SD: 7.6+/−0.48 cm).

In order to allow for characterization of the deposition, the nose region was segmented into four rectangular nasal regions, namely, a lower anterior region (LowAnt), an upper anterior region (UpAnt), a lower posterior region (LowPost) and an upper posterior region (UpPost), and one pharyngeal region. The horizontal segmentation was fixed at a distance of 19 mm (4 pixels) from the nasal floor as determined from the most intense contour in the gradient image, and approximates the lower border of the middle turbinate. The vertical segmentation was fixed at a distance of 38 mm (8 pixels) anterior to the transition between the nose and nasopharynx, as visible in the cumulative images and lies between the nasal valve and head of the middle turbinate. Because of the limited spatial resolution of the camera system, the lower regions were extended caudally and the upper regions cranially, in order to include all counts originating from activity within the respective regions.

Figure 12B:
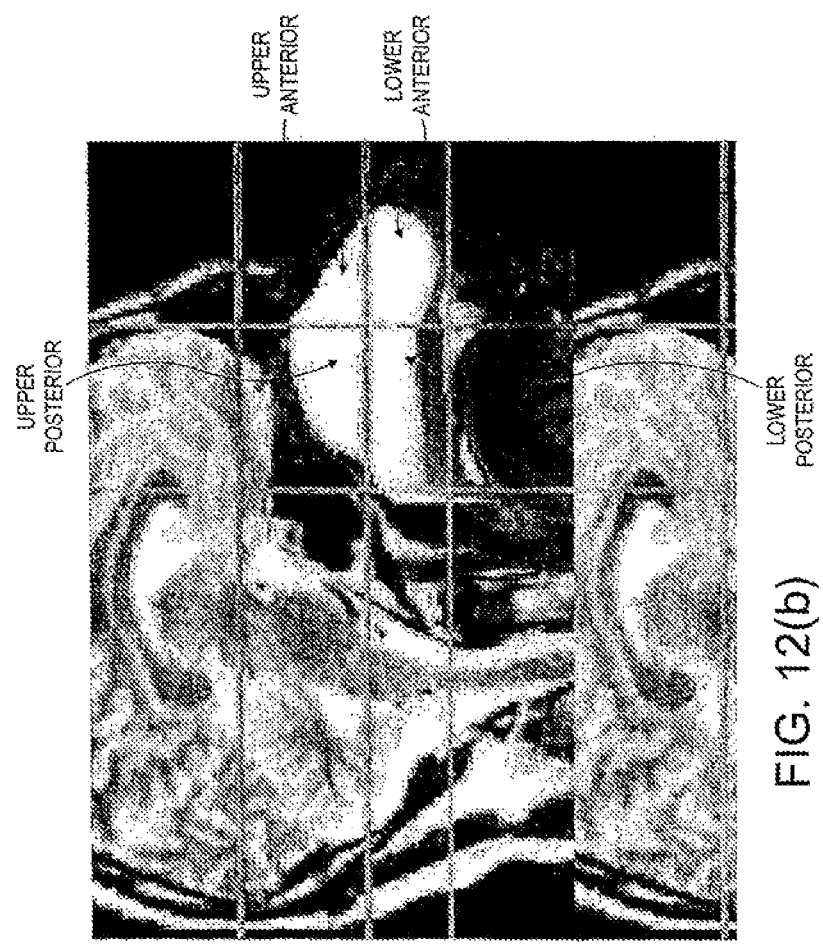
FIG. 12(b) illustrates the cumulative deposition by obtained by the bi-directional administration system as employed in Example #2.

FIGS. 12(a) and 12(b) illustrate respectively the cumulative deposition as obtained by the two administration systems, with FIG. 12(a) illustrating the cumulative deposition as obtained by the conventional nasal spray administration system and FIG. 12(b) illustrating the cumulative deposition as obtained by the bi-directional administration system.

As will be clearly seen, the bi-directional administration system provides for a much greater fraction of the deposition to the upper posterior region as compared to the conventional nasal spray administration system.

Table II below shows the measured values for the initial deposition in the four nasal segments and the nasopharynx, as represented by the first in the series of images for each of the subjects.

TABLE II

| Image | Conventional Mean | Conventional SD | Conventional CV | Conventional Nasal % | Conventional All % | Inventive Mean | Inventive SD | Inventive CV | Inventive Nasal % | Inventive All % | Difference P-value |
|---|---|---|---|---|---|---|---|---|---|---|---|
| Upper Anterior | 32704 | 20205 | 0.62 | 43 | 38 | 12991 | 8095 | 0.62 | 19 | 17 | p < 0.02 |
| Lower Anterior | 24172 | 14099 | 0.58 | 32 | 28 | 9228 | 6184 | 0.67 | 13 | 12 | p < 0.004 |
| Upper Posterior | 8346 | 7242 | 0.87 | 11 | 10 | 22083 | 7599 | 0.34 | 32 | 28 | p < 0.004 |
| Lower Posterior | 10983 | 7840 | 0.71 | 14 | 13 | 24997 | 8468 | 0.34 | 36 | 32 | p < 0.02 |
| Nasopharynx | 8899 | 10469 | 1.18 |  | 10 | 8992 | 7871 | 0.88 |  | 11 | NS |
| Sum Nasal Regions | 76205 | 21448 | 0.28 |  |  | 69299 | 8635 | 0.12 |  |  | NS |
| Sum All Regions | 85104 | 14716 | 0.17 |  |  | 78290 | 8566 | 0.11 |  |  | NS |

FIG. 13 graphically illustrates the mean deposition fractions in the four segmented nasal regions for both the conventional nasal spray administration system and the bi-directional administration system.

As can be seen, the bi-directional administration system provides for initial deposition of 68% to the posterior nasal segments beyond the nasal valve of the total dose as deposited in the nasal cavity, whereas only 25% of the total dose as deposited in the nasal cavity is initially deposited in these segments following delivery with the conventional nasal spray administration system. In particular, following administration, the conventional nasal spray administration system provides for initial deposition of only 11% (SD 10%) of the total dose as deposited in the nasal cavity in the upper posterior region of the nasal cavity, whereas the bi-directional administration system provides for initial deposition of 32% (SD 11%) of the total dose as deposited in the nasal cavity in the upper posterior region of the nasal cavity.

The results of this study thus support the postulation of the present inventors that the increased concentration of the delivered substance to the CNS for any given blood plasma concentration could at least in part be a function of the relative fractions of substance which are delivered to the anterior and posterior regions of the nasal cavity, and in particular the upper posterior region.

EXAMPLE #3

The purpose of this study was to characterize the deposition as achieved by powder aerosol and liquid jet administration systems in accordance with embodiments of the present invention.

In this study, nine healthy subjects, 4 females and 5 males, were studied.

In separate sessions, the subjects received a test substance by one of three different nasal administration systems, these being:
 (i) a conventional nasal spray administration system in which a labeled test solution was conventionally nasally administered using a single-dose spray pump as supplied by Ing Erich Pfeiffer GmbH (Radolfsee, Germany) which is specified to generate a liquid spray with a mean particle size of 43 μm, with 100 μl of the test solution being delivered to one nostril;
(ii) the bi-directional administration system of the first-described embodiment where configured to deliver a labeled test powder from a conventional gelatine capsule, with approximately 4 mg of the test powder being nasally administered to one nostril; and
(iii) the bi-directional administration system of the first-described embodiment where incorporating the same single-dose spray pump as the conventional nasal spray administration system but with the nozzle modified, here truncated, to deliver a liquid jet, in which a labeled test solution was nasally administered, with 100 μl of the test solution being delivered to one nostril.

The three study sessions were performed two days apart to secure complete washout and decay.

The test solution was a $^{99m}$Tc-DTPA solution, which was made by adding 120-150 MBq $^{99m}$TcO$_4^-$ (IFETEC generator) as supplied by Isopharma (Kjeller, Norway) in 6 ml of eluate to a vial containing freeze-dried diethylene triamine pentaacetic acid DTPA as supplied by Isopharma (Kjeller, Norway).

The test powder was a $^{99m}$Tc-labelled powder as supplied by the Institute for Energy Technology (IFE) (Kjeller, Norway).

The deposition of the test solution and powder in the nasal cavity was imaged using a scintillation camera system, here a VERTEX camera as supplied by ADAC Laboratories (USA) which was equipped with a low energy parallel hole high resolution VXGP collimator.

The test samples were administered with the subjects sitting in the upright position, and, following administration, the subjects each turned their head to the side and positioned their cheek and the tip of their nose in an alignment device which was attached to the camera. In this study, the floor of the nasal cavity was projected close to the horizontal, corresponding to the x-axis of the camera detector. This re-positioning took between approximately 10 and 30 seconds from the dose administration and imaging was initiated immediately thereafter. A total of 16 images, each containing 128×128 pixels, were acquired at two minute intervals. The subjects were instructed not to sniff during the imaging procedure.

As a consequence of the variation in administered activity, the acquired images were normalized so that the first image in each series, which represents the initial deposition, had a total image intensity equal to 100,000 within a region drawn around the nose as appearing in the cumulative images. As the floor of the nose and the curvature of the pharynx were clearly visible in the cumulative images as derived from each of the series, each series of images could conveniently be aligned.

Nasal dimensions were measured by acoustic rhinometry using Rhin2000 anatomic nose adaptors as supplied by RhinoMetrics (Lynge, Denmark), to verify normal nasal dimensions and to assist in nasal segmentation.

In order to allow for characterization of the deposition, the nose region was segmented into four rectangular nasal regions, namely, a lower anterior region (LowAnt), an upper anterior region (UpAnt), a lower posterior region (LowPost) and an upper posterior region (UpPost), and one pharyngeal region. The horizontal segmentation was fixed at a distance of approximately 19 mm (4 pixels) from the nasal floor as determined from the most intense contour in the gradient image, and approximates the lower border of the middle turbinate. The vertical segmentation was fixed at a distance of approximately 38 mm (8 pixels) anterior to the transition between the nose and nasopharynx, as visible in the cumulative images and lies between the nasal valve and head of the middle turbinate. Because of, the limited spatial resolution of the camera system, the lower regions were extended caudally and the upper regions cranially, in order to include all counts originating from activity within the respective regions.

Tables III(a) to (c) below show the measured values for the initial deposition in the four nasal segments and the nasopharynx, as represented by the first in the series of images for each of the subjects, for each of the administration systems.

TABLE III(a)

| Image | Conventional Mean | Conventional SD | Conventional CV | Conventional Nasal % | Conventional All % |
|---|---|---|---|---|---|
| Upper Anterior | 25565 | 16531 | 0.65 | 26 | 26 |
| Lower Anterior | 31935 | 26981 | 0.84 | 33 | 32 |
| Upper Posterior | 12893 | 8377 | 0.65 | 13 | 13 |
| Lower Posterior | 27999 | 19622 | 0.70 | 28 | 28 |
| Nasopharynx | 1579 | 4293 | 2.72 | | 1 |
| Sum Nasal Regions | 98392 | | | | |
| Sum All Regions | 99971 | | | | |

TABLE III(b)

| Image | Liquid Jet Mean | Liquid Jet SD | Liquid Jet CV | Liquid Jet Nasal % | Liquid Jet All % |
|---|---|---|---|---|---|
| Upper Anterior | 13993 | 8493 | 0.61 | 15 | 14 |
| Lower Anterior | 8409 | 7893 | 0.94 | 9 | 8 |
| Upper Posterior | 47518 | 9150 | 0.19 | 52 | 48 |
| Lower Posterior | 21598 | 11179 | 0.52 | 24 | 22 |
| Nasopharynx | 8105 | 10310 | 1.27 | | 8 |
| Sum Nasal Regions | 91518 | | | | |
| Sum All Regions | 99623 | | | | |

TABLE III(c)

| Image | Powder Mean | Powder SD | Powder CV | Powder Nasal % | Powder All % |
|---|---|---|---|---|---|
| Upper Anterior | 20019 | 13147 | 0.66 | 21 | 20 |
| Lower Anterior | 8115 | 5445 | 0.67 | 8 | 8 |
| Upper Posterior | 54281 | 14196 | 0.26 | 56 | 54 |
| Lower Posterior | 14917 | 10682 | 0.72 | 15 | 15 |
| Nasopharynx | 2515 | 3501 | 1.39 | | 3 |
| Sum Nasal Regions | 97332 | | | | |
| Sum All Regions | 99847 | | | | |

FIG. 14 graphically illustrates the mean deposition fractions in the four segmented nasal regions for both the conventional nasal spray administration system and the bi-directional administration systems.

As can be seen, the bi-directional liquid jet administration system provides for initial deposition of 76 °A, of the dose as initially deposited in the nasal cavity to the posterior segments beyond the nasal valve and the powder administration system provides for initial deposition of 71% of the dose as initially deposited in the nasal cavity to the posterior segments beyond the nasal valve, whereas the conventional nasal spray administration system provides for initial deposition of only about 41% of the dose as initially deposited in the nasal cavity in these segments. In particular, following administration, the conventional nasal spray administration system provides for initial deposition of only about 13% of the dose as initially deposited in the nasal cavity in the upper posterior region of the nasal cavity, whereas the bi-directional liquid jet administration system provides for initial deposition of about 52% (SD 9%) of the dose as initially deposited in the nasal cavity to the upper posterior region of the nasal cavity and the bi-directional powder administration system provides for initial deposition of about 56% (SD 14%) of the dose as initially deposited in the nasal cavity to the upper posterior region of the nasal cavity.

The results of this study thus support the postulation of the present inventors that the increased concentration of the delivered substance to the CNS for any given blood plasma concentration could at least in part be a function of the relative fractions of substance which are delivered to the anterior and posterior regions of the nasal cavity, and in particular the upper posterior region.

Finally, it will be understood that the present invention has been described in its preferred embodiments and can be modified in many different ways without departing from the scope of the invention as defined by the appended claims.

REFERENCES

1. Born, J et al, Sniffing neuropeptides: a transnasal approach to the human brain, Nature Neuroscience, 2002, pages 514 to 516.
2. Cole, P, The Respiratory Role of the Upper Airway, Mosby, 1992, pages 7 and 8.
3. Einer-Jensen, N et al, Local transfer of diazepam, but not of cocaine, from the nasal cavities to the brain arterial blood in rats, Pharmacol and Toxicol, 2000, Vol 87, pages 276 to 278.
4. Einer-Jensen, N et al, Transfer of titrated water, tyrosine and propanol from the nasal cavity to cranial arterial blood in rats, Experimental Brain Research, 2000, vol 130, pages 216 to 220.
5. Martens, J et al, Simultaneous determination of midazolam and its metabolites 1-hydroxymidazolam and 4-hydroxymidazolam in human serum using gas chromatography-mass spectrometry, Journal of Chromatography B, 1997, Vol 692, pages 95 to 100.
6. Rosenberger, H, Growth and Development of the Naso-Respiratory Area in Childhood, PhD Thesis, Laboratory of Anatomy, School of Medicine, Western Reserve University, Presented to the Annual Meeting of the American Laryngological, Rhinological and Otological Society, Charleston, South Carolina, USA, 1934.
7. Zacharek, M A et al, Sagittal and Coronal Dimensions of the Ethmoid Roof: A Radioanatomic Study, Am J Rhinol 2005, Vol 19, pages 348 to 352.

The above references are herein incorporated in their entirety by reference.

The invention claimed is:

1. A method of treating a subject by delivering a pharmaceutical composition to a nasal airway of the subject, comprising:
    fitting a mouthpiece to a mouth of the subject;
    fitting a nosepiece unit to a first nostril of the subject, wherein the nosepiece unit comprises:
        a nosepiece which is configured to guide the nosepiece unit into a first nasal passageway of the subject;
        a delivery channel which is fluidly connected between the mouthpiece and the nosepiece, such that an exhalation air flow can be delivered from the mouthpiece through the delivery channel, and through the nosepiece when the subject exhales through the mouthpiece; and
        a supply unit which is configured to deliver a dose of the pharmaceutical composition;
    exhaling with an exhalation breath of the subject through the mouthpiece to cause closure of an oropharyngeal velum of the subject, wherein the exhalation breath of the subject produces the exhalation air flow which exceeds a predetermined flow rate and flows through the first nostril of the subject and into the first nasal passageway of the subject, around a posterior margin of a nasal septum of the subject and into a second nasal passageway of the subject, and out of a second nostril of the subject;
    delivering, during a time when the exhalation breath of the subject produces the exhalation air flow, the dose of the pharmaceutical composition to the nasal airway of the subject such that at least 30% of the dose of the pharmaceutical composition, as initially deposited in the nasal airway of the subject, is deposited at an upper posterior region of the nasal airway of the subject, which is posterior of a nasal valve of the subject and above an inferior meatus of the subject.

2. The method of claim 1, wherein the pharmaceutical composition is an aerosol spray.

3. The method of claim 2, wherein the aerosol spray is a liquid.

4. The method of claim 2, wherein the aerosol spray is a powder.

5. The method of claim 1, wherein the pharmaceutical composition is a liquid jet.

6. The method of claim 1, wherein the pharmaceutical composition is a dopamine agonist.

7. The method of claim 1, wherein the pharmaceutical composition is a triptan.

8. The method of claim 7, wherein the triptan is sumatriptan.

9. The method of claim 1, wherein the pharmaceutical composition has activity on a learning pathway.

10. The method of claim 1, wherein the pharmaceutical composition comprises vasopressin or its pharmaceutically-acceptable derivatives or analogues.

11. The method of claim 1, wherein the pharmaceutical composition comprises desmopressin or its pharmaceutically-acceptable derivatives or analogues.

12. The method of claim 1, wherein the pharmaceutical composition is an acetylcholinesterase inhibitor.

13. The method of claim 1, wherein the pharmaceutical composition comprises rivastigmine or its pharmaceutically-acceptable derivatives or analogues.

14. A method of treating a subject by delivering a pharmaceutical composition to a nasal airway of the subject, comprising:

fitting a mouthpiece to a mouth of the subject;
fitting a nosepiece unit to a first nostril of the subject, wherein the nosepiece unit comprises:
- a nosepiece which is configured to guide the nosepiece unit into a first nasal passageway of the subject;
- a delivery channel which is fluidly connected between the mouthpiece and the nosepiece, such that an exhalation air flow can be delivered from the mouthpiece through the delivery channel, and through the nosepiece when the subject exhales through the mouthpiece; and
- a supply unit which is configured to deliver a dose of the pharmaceutical composition;

exhaling with an exhalation breath of the subject through the mouthpiece to cause closure of an oropharyngeal velum of the subject, wherein the exhalation breath of the subject produces the exhalation air flow which exceeds a predetermined flow rate and flows through the first nostril of the subject and into the first nasal passageway of the subject, around a posterior margin of a nasal septum of the subject and into a second nasal passageway of the subject, and out of a second nostril of the subject;

delivering, during a time when the exhalation breath of the subject produces the exhalation air flow, the dose of the pharmaceutical composition to the nasal airway of the subject such that at least 40% of the dose of the pharmaceutical composition, as initially deposited in the nasal airway of the subject, is deposited at an upper posterior region of the nasal airway of the subject, which is posterior of a nasal valve of the subject and above an inferior meatus of the subject.

15. The method of claim 14, wherein the pharmaceutical composition is an aerosol spray.

16. The method of claim 15, wherein the aerosol spray is a liquid.

17. The method of claim 15, wherein the aerosol spray is a powder.

18. The method of claim 14, wherein the pharmaceutical composition is a liquid jet.

19. The method of claim 14, wherein the pharmaceutical composition is a dopamine agonist.

20. The method of claim 14, wherein the pharmaceutical composition is a triptan.

21. The method of claim 20, wherein the triptan is sumatriptan.

22. The method of claim 14, wherein the pharmaceutical composition has activity on a learning pathway.

23. The method of claim 14, wherein the pharmaceutical composition comprises vasopressin or its pharmaceutically-acceptable derivatives or analogues.

24. The method of claim 14, wherein the pharmaceutical composition comprises desmopressin or its pharmaceutically-acceptable derivatives or analogues.

25. The method of claim 14, wherein the pharmaceutical composition is an acetylcholinesterase inhibitor.

26. The method of claim 14, wherein the pharmaceutical composition comprises rivastigmine or its pharmaceutically-acceptable derivatives or analogues.

27. A method of treating a subject by delivering a pharmaceutical composition to a nasal airway of the subject, comprising:

fitting a mouthpiece to a mouth of the subject;
fitting a nosepiece unit to a first nostril of the subject, wherein the nosepiece unit comprises:
- a nosepiece which is configured to guide the nosepiece unit into a first nasal passageway of the subject;
- a delivery channel which is fluidly connected between the mouthpiece and the nosepiece, such that an exhalation air flow can be delivered from the mouthpiece through the delivery channel, and through the nosepiece when the subject exhales through the mouthpiece; and
- a supply unit which is configured to deliver a dose of the pharmaceutical composition;

exhaling with an exhalation breath of the subject through the mouthpiece to cause closure of an oropharyngeal velum of the subject, wherein the exhalation breath of the subject produces the exhalation air flow which exceeds a predetermined flow rate and flows through the first nostril of the subject and into the first nasal passageway of the subject, around a posterior margin of a nasal septum of the subject and into a second nasal passageway of the subject, and out of a second nostril of the subject;

delivering, during a time when the exhalation breath of the subject produces the exhalation air flow, the dose of the pharmaceutical composition to the nasal airway of the subject such that at least 50% of the dose of the pharmaceutical composition, as initially deposited in the nasal airway of the subject, is deposited at an upper posterior region of the nasal airway of the subject, which is posterior of a nasal valve of the subject and above an inferior meatus of the subject.

28. The method of claim 27, wherein the pharmaceutical composition is an aerosol spray.

29. The method of claim 28, wherein the aerosol spray is a liquid.

30. The method of claim 28, wherein the aerosol spray is a powder.

31. The method of claim 27, wherein the pharmaceutical composition is a liquid jet.

32. The method of claim 27, wherein the pharmaceutical composition is a dopamine agonist.

33. The method of claim 27, wherein the pharmaceutical composition is a triptan.

34. The method of claim 33, wherein the triptan is sumatriptan.

35. The method of claim 27, wherein the pharmaceutical composition has activity on a learning pathway.

36. The method of claim 27, wherein the pharmaceutical composition comprises vasopressin or its pharmaceutically-acceptable derivatives or analogues.

37. The method of claim 27, wherein the pharmaceutical composition comprises desmopressin or its pharmaceutically-acceptable derivatives or analogues.

38. The method of claim 27, wherein the pharmaceutical composition is an acetylcholinesterase inhibitor.

39. The method of claim 27, wherein the pharmaceutical composition comprises rivastigmine or its pharmaceutically-acceptable derivatives or analogues.

* * * * *